(12) United States Patent
Hakkinen

(10) Patent No.: US 6,852,722 B2
(45) Date of Patent: Feb. 8, 2005

(54) COMPOSITIONS AND METHODS FOR STIMULATING GASTROINTESTINAL MOBILITY

(75) Inventor: John Hakkinen, N. Stonington, CT (US)

(73) Assignee: Pfizer Inc., New York, NY (US)

(*) Notice: Subject to any disclaimer, the term of this patent is extended or adjusted under 35 U.S.C. 154(b) by 15 days.

(21) Appl. No.: 10/411,756

(22) Filed: Apr. 11, 2003

(65) Prior Publication Data

US 2003/0225096 A1 Dec. 4, 2003

Related U.S. Application Data

(62) Division of application No. 09/870,105, filed on May 30, 2001, now Pat. No. 6,548,501.
(60) Provisional application No. 60/208,234, filed on May 31, 2000.

(51) Int. Cl.[7] .................... A61K 31/495; A61K 31/53; A61K 31/50; A61K 31/517; A61K 31/44
(52) U.S. Cl. .................... 514/249; 514/241; 514/248; 514/250; 514/258.1; 514/303
(58) Field of Search .................... 514/249, 250, 514/303, 256, 258, 291, 262.2

(56) References Cited

U.S. PATENT DOCUMENTS

| | | | |
|---|---|---|---|
| 4,962,115 A | 10/1990 | Van Daele | 514/326 |
| 6,251,902 B1 | 6/2001 | Carpino et al. | 514/249 |
| 6,376,509 B1 | 4/2002 | Bakshi et al. | 514/303 |

FOREIGN PATENT DOCUMENTS

| | | | | |
|---|---|---|---|---|
| WO | WO 9724369 | 7/1997 | ............ | C07K/5/06 |
| WO | WO 9858947 | 12/1998 | ............ | C07K/5/023 |
| WO | WO 9858949 | 12/1998 | ............ | C07K/5/06 |

OTHER PUBLICATIONS

Smith, et al. "Peptidomimetic Regulation of Growth Hormone Secretion", *Endocrine Reviews* 18(5), pp. 621–645 (1997).
Ankersen, et al., "Growth hormone secretagogues: recent advances and applications", *DDT* 4(11), pp. 497–506 (1999).
Casanueva, et al., "Growth Hormone Secretagogues: Physiological Role and Clinical Utility", *TEM* 10(1), pp. 30–38 (1999).

Shulman, "Gastrointestinal Effects of Growth Hormone", *Endocrine* 12(2), pp. 147–152 (2000).
Feighner, et al., "Receptor for Motilin Identified in the Human Gastrointestinal System", *Science* 284, pp. 2184–2188 (1999).
Faghih, et al., "Motilides and motilactides: design and development of motilin receptor agonists as a new class of gastrointestinal prokinetic drugs", *Science* 23(8), pp. 861–872 (1998).
Kirst, et al., "Recent developments with macrolide antibiotics", *Exp. Opin. Ther. Patents* 8(2), pp. 111–120 (1998).
Kojima, et al., "Ghrelin is a growth–hormone–releasing acylated peptide from stomach", *Nature* 402, pp. 656–660 (1999).
Slonim, et al. "A Preliminary Study of Growth Hormone Therapy for Crohn's Disease", *The New England Journal of Medicine* 342(22), pp. 1633–1637 (2000).
Faghih, et al., "Synthesis of 9–Deoxo–4–deoxy–6,9–epoxy-erythromycin Derivatives: Novel and Acid–Stable Motilides", *J. Med. Chem.* 41, pp. 3402–3408 (1998).
Masuda, et al., "Ghrelin Stimulates Gastric Acid Secretion and Motility in Rats", *Biochem and Biophys. Res. Comm.* 276, pp. 905–908 (2000).
Svensson, et al., "Clinical and Experimental Effects of Growth Hormone Secretagogues on Various Organ Systems", *Horm Res* 51 (suppl 3), pp. 16–20 (1999).

*Primary Examiner*—Kevin E. Weddington
(74) *Attorney, Agent, or Firm*—John A. Wichtowski; Todd M. Crissey

(57) ABSTRACT

The present invention is directed to methods for stimulating the motility of the gastrointestinal system in a patient which comprises administering a growth hormone secretagogue, a prodrug thereof or a pharmaceutically acceptable salt of said secretagogue or said prodrug. More particularly, the present invention provides methods for stimulating the motility of the gastrointestinal system in a patient which comprises administering a compound of Formula I:

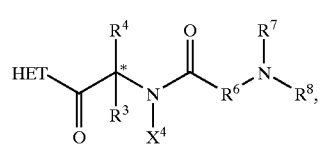

a prodrug thereof or a pharmaceutically acceptable salt of said secretagogue or said prodrug.

9 Claims, No Drawings

COMPOSITIONS AND METHODS FOR STIMULATING GASTROINTESTINAL MOBILITY

CROSS REFERENCE TO RELATED APPLICATION

This is a divisional application of U.S. Ser. No. 09/870,105, filed May 30, 2001, now U.S. Pat. No. 6,548,501, which claims the benefit of U.S. provisional application No. 60/208,234, filed May 31, 2000.

FIELD OF THE INVENTION

The present invention provides methods of using growth hormone secretagogues, prodrugs thereof and pharmaceutically acceptable salts of said secretagogues and said prodrugs, as stimulators of the motility of the gastrointestinal system in patients. More specifically, the present invention provides methods of using compounds of Formula I below as stimulators of the motility of the gastrointestinal system in patients. In addition, the present invention provides methods of treating conditions of impaired gastrointestinal motility, such as gastroesophageal reflux disease, gastroparesis (e.g., as a complication of diabetes), emesis (e.g., that caused by cancer chemotherapy agents), postoperative ileus, constipation (e.g., that associated with the hypomotility phase of irritable bowel syndrome) and colonic pseudo-obstruction. The present invention also provides pharmaceutical compositions and kits for the above uses.

BACKGROUND OF THE INVENTION

Gastrointestinal (GI) motility is a coordinated neuromuscular process that transports nutrients through the digestive system. C. Scarpignato, Dig. Dis. 15: 112 (1997). Impaired GI motility, which may be involved in gastroesophageal reflux disease, gastroparesis (e.g., diabetic and postsurgical), irritable bowel syndrome and constipation, is one of the largest health care burdens of industralized nations. S. D. Feighner et al., Science 284: 2184–2188 (Jun. 25, 1999). Impaired GI motility can also lead to emesis (e.g., that caused by cancer chemotherapy agents), postoperative ileus and colonic pseudo-obstruction.

Very few compounds are known in the art to be useful for treating impaired GI motility. For example, PROPULSID® which contains cisapride monohydrate is an oral gastrointestinal agent (see U.S. Pat. No. 4,962,115). It is indicated for the symptomatic treatment of adult patients with nocturnal heartburn due to gastroesophageal reflux disease. Other prokinetic agents include, for example, metoclopramide, erythromycin, domperidone, ondansetron, tropisetron, mosapride and itopride. However, these therapeutic regimens suffer from numerous problems. For instance, PROPULSID® was recently removed from the market due to its potential to induce cardiac arrhythmias. A more effective, physiological way to stimulate GI motility would be highly desirable.

Growth hormone, which is secreted from the pituitary, stimulates growth of all tissues of the body that are capable of growing. In addition, growth hormone is known to have the following basic effects on the metabolic processes of the body: (1) increased rate of protein synthesis in all cells of the body; (2) decreased rate of carbohydrate utilization in cells of the body; and (3) increased mobilization of free fatty acids and use of fatty acids for energy. As is known to those skilled in the art, the known and potential uses of growth hormone are varied and multitudinous. See "Human Growth Hormone," Strobel and Thomas, Pharmacological Reviews, 46, pg. 1–34 (1994). Also, these varied uses of growth hormone are summarized in International Patent Application, Publication Number WO 97/24369.

Various ways are known to release growth hormone (see Recent Progress in Hormone Research, vol. 52, pp. 215–245 (1997); and Front Horm Res. Basel, Karger, vol. 24, pp. 152–175 (1999)). For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase secretion of growth hormone releasing factor (GRF) or ghrelin (see Nature, vol. 402, pp. 656–660 (Dec. 9, 1999)), or all of these.

In cases where increased levels of growth hormone were desired, the problem was generally solved by providing exogenous growth hormone or by administering GRF, IGF-1 or a peptidyl compound which stimulated growth hormone production and/or release. In any case, the peptidyl nature of the compound necessitated that it be administered by injection. Initially, the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection. In addition, administration of exogenous growth hormone may result in side-effects, including edema, and does not correlate with the pulsatile release seen in the endogenous release of growth hormone.

Certain compounds have been developed which stimulate the release of endogenous growth hormone. Peptides which are known to stimulate the release of endogenous growth hormone include growth hormone releasing hormone and its analogs, the growth hormone releasing peptides, GHRP-6 and GHRP-1 (described in U.S. Pat. No. 4,411,890; International Patent Application, Publication No. WO 89/07110; and International Patent Application, Publication No. WO 89/07111), and GHRP-2 (described in International Patent Application, Publication No. WO 93/04081), as well as hexarelin (J. Endocrinol. Invest., 15 (Suppl. 4): 45 (1992)). Other compounds possessing growth hormone secretagogue activity are disclosed in the following International Patent Applications (listed by Publication Nos.), issued U.S. Patents and published European Patent Applications: WO 98/46569, WO 98/51687, WO 98/58947, WO 98/58949, WO 98/58950, WO 99/08697, WO 99/09991, WO 95/13069, U.S. Pat. Nos. 5,492,916, 5,494,919, WO 95/14666, WO 94/19367, WO 94/13696, WO 94/11012, U.S. Pat. No. 5,726,319, WO 95/11029, WO 95/17422, WO 95/17423, WO 95/34311, WO 96/02530, WO 96/22996, WO 96/22997, WO 96/24580, WO 96/24587, U.S. Pat. No. 5,559,128, WO 96/32943, WO 96/33189, WO 96/15148, WO 96/38471, WO 96/35713, WO 97/00894, WO 97/07117, WO 97/06803, WO 97/11697, WO 97/15573, WO 97/22367, WO 97/23508, WO 97/22620, WO 97/22004, WO 97/21730, WO 97/24369, U.S. Pat. No. 5,663,171, WO 97/34604, WO 97/36873, WO 97/40071, WO 97/40023, WO 97/41878, WO 97/41879, WO 97/46252, WO 97/44042, WO 97/38709, WO 98/03473, WO 97/43278, U.S. Pat. Nos. 5,721,251, 5,721,250, WO 98/10653, U.S. Pat. Nos. 5,919,777, 5,830,433 and EP 0995748.

In addition, the following growth hormone secretagogues are known in the art: MK-0677, L-162752 and L-163022 (Merck); NN703 and ipamorelin (Novo Nordisk); hexarelin (Pharmacia & Upjohn); GPA-748 (KP102, GHRP-2) (American Home Products); and LY444711 (Eli Lilly). The following agents that stimulate GH release via GHRH/GRF receptor (including GHRH/GRF derivatives, analogs and mimetics) are known in the art: Geref (Ares/Serono); GHRH (1-44) (BioNebraska); Somatorelin (GRF 1-44) (Fujisawa/ICN); and ThGRF (Theratechnologies).

Endocrine Reviews 18(5): 621–645 (1997) provides an overview of peptidomimetic regulation of growth hormone secretion by growth hormone secretagogues. Horm. Res. 1999; 51 (suppl 3):16–20 (1999), examines the clinical and experimental effects of growth hormone secretagogues on various organ systems. Drug Discovery Today, Vol. 4, No. 11, November 1999; and TEM Vol. 10, No. 1, 1999, disclose potential therapeutic applications of growth hormone secretagogues, including their use in treating growth hormone disorders such as growth hormone deficiency (GHD), age-related conditions, obesity and catabolic conditions, and their use in sleep enhancement.

International Patent Applications, Publication Nos. WO 97/24369 and WO 98/58947 disclose that certain growth hormone secretagogues are useful for the treatment or prevention of osteoporosis, congestive heart failure, frailty associated with aging, obesity; accelerating bone fracture repair, attenuating protein catabolic response after a major operation, reducing cachexia and protein loss due to chronic illness, accelerating wound healing or accelerating the recovery of burn patients or patients having undergone major surgery; improving muscle strength, mobility, maintenance of skin thickness, metabolic homeostasis or renal homeostasis. Published European patent application 0995748 discloses that certain dipeptide growth hormone secretagogues are useful for the treatment or prevention of musculoskeletal frailty, including osteoporosis.

The administration of a growth hormone secretagogue is also known to enhance the quality of sleep, which is disclosed in International Patent Application, Publication No. WO 97/24369. A growth hormone secretagogue can be administered to a patient having or at risk of having one or more of the conditions or symptoms recited above. Commonly assigned U.S. nonprovisional patent application Ser. No. 09/290985, filed Apr. 13, 1999, discloses pharmaceutical compositions comprising certain $\beta_3$ adrenergic agonists and growth hormone secretagogues or growth hormone, and their use for treating diabetes, obesity, hyperglycemia, frailty associated with obesity or frailty associated with aging, and for enhancing the quality of sleep in a mammal. International Patent Application, Publication No. WO 98/58949, discloses the treatment of insulin resistance with certain growth hormone secretagogues.

Abstract OR4-5 from The Endocrine Society $81^{st}$ Annual Meeting (12–15 June 1999), San Diego, Calif., discloses that growth hormone (GH) therapy resulted in marked clinical improvement in patients with active Crohn's disease (regional inflammation of the intestines).

S. D. Feighner et al., Science 284: 2184–2188 (Jun. 25, 1999), discloses that a heterotrimeric guanosine triphosphate-binding protein (G protein)-coupled receptor for motilin (a 22-amino acid peptide hormone expressed throughout the gastrointestinal tract of humans and other species) was isolated from the human stomach, and that its amino acid sequence was found to be 52 percent identical to the human receptor for growth hormone secretagogues.

SUMMARY OF THE INVENTION

The present invention provides a method of stimulating the motility of the gastrointestinal system in a patient which comprises administering to the patient a gastrointestinal motility stimulating effective amount of a growth hormone secretagogue.

More particularly, it provides such method wherein the growth hormone secretagogue is an orally active growth hormone secretagogue. Even more particularly, it provides such method wherein the growth hormone secretagogue is orally administered.

More particularly, it provides such method wherein the growth hormone secretagogue is a non-peptidyl growth hormone secretagogue.

More particularly, it provides such method wherein the patient is a human.

The present invention provides a method of stimulating the motility of the gastrointestinal system in a patient which comprises administering to the patient a gastrointestinal motility stimulating effective amount of a compound of the Formula I:

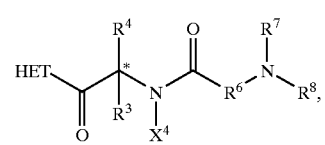

or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, or a tautomer thereof, wherein HET is a heterocyclic moiety selected from the group consisting of

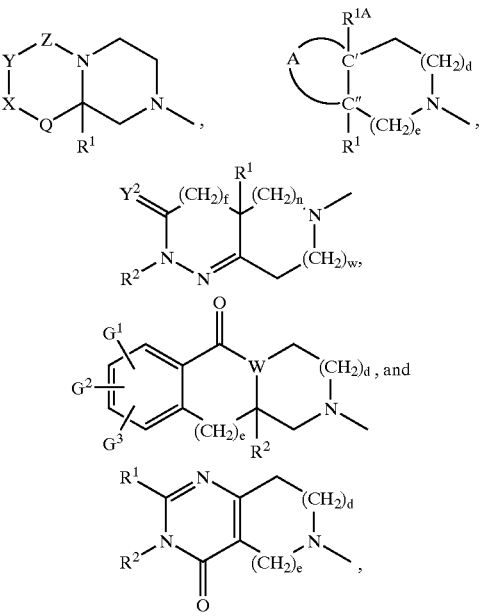

d is 0, 1 or 2;
e is 1 or 2;
f is 0 or 1;

n and w are 0, 1 or 2, provided that n and w cannot both be 0 at the same time;

$Y^2$ is oxygen or sulfur;

A is a divalent radical, where the left hand side of the radical as shown below is connected to C" and the right hand side of the radical as shown below is connected to C', selected from the group consisting of
—$NR^2$—C(O)—$NR^2$—, —$NR^2S(O)_2$—$NR^2$, —O—C(O)—$NR^2$, —$NR^2$—C(O)—O—, —C(O)—$NR^2$—C(O)—, —C(O)—$NR^2$—C($R^9R^{10}$)—, —C($R^9R^{10}$)—$NR^2$—C(O)—, —C($R^9R^{10}$)—C($R^9R^{10}$)—C($R^9R^{10}$)—, —S(O)$_2$—C($R^9R^{10}$)—C($R^9R^{10}$)—, —C($R^9R^{10}$)—O—C(O)—, —C($R^9R^{10}$)—O—C($R^9R^{10}$)—, —$NR^2$—C(O)—C($R^9R^{10}$)—, —O—C(O)—C($R^9R^{10}$)—, —C($R^9R^{10}$)—C(O)—$NR^2$—, —C($R^9R^{10}$)—C(O)—O—, —C(O)—$NR^2$—C($R^9R^{10}$)—C($R^9R^{10}$)—, —C(O)—O—C($R^9R^{10}$)—, —C($R^9R^{10}$)—C($R^9R^{10}$)—C($R^9R^{10}$)—, —S(O)$_2$—$NR^2$—C($R^9R^{10}$)—C($R^9R^{10}$)—, —C($R^9R^{10}$)—C($R^9R^{10}$)—$NR^2$—C(O)—, —C($R^9R^{10}$)—C($R^9R^{10}$)—O—C(O)—, —$NR^2$—C(O)—C($R^9R^{10}$)—C($R^9R^{10}$)—, —$NR^2$—S(O)$_2$—C($R^9R^{10}$)—C($R^9R^{10}$)—, —O—C(O)—C($R^9R^{10}$)—C($R^9R^{10}$)—, —C($R^9R^{10}$)—C($R^9R^{10}$)—C(O)—$NR^2$—, —C($R^9R^{10}$)—C($R^9R^{10}$)—C(O)—, —C($R^9R^{10}$)—$NR^2$—C(O)—O—, —C($R^9R^{10}$)—O—C(O)—$NR^2$, —C($R^9R^{10}$)—$NR^2$—C(O)—$NR^2$, —$NR^2$—C(O)—C($R^9R^{10}$)—, —$NR^2$—C(O)—$NR^2$—C($R^9R^{10}$)—, —O—C(O)—$NR^2$—C($R^9R^{10}$)—, —C(O)—N=C($R^{11}$)—$NR^2$—, —C(O)—$NR^2$—C($R^{11}$)=N—, —C($R^9R^{10}$)—$NR^{12}$—C($R^9R^{10}$)—, —$NR^{12}$—C($R^9R^{10}$)—, —$NR^{12}$—C($R^9R^{10}$)—C($R^9R^{10}$)—, —C(O)—O—C($R^9R^{10}$)—C($R^9R^{10}$)—, —$NR^2$—C($R^{11}$)=N—C(O)—, —C($R^9R^{10}$)—C($R^9R^{10}$)—N($R^{12}$)—, —C($R^9R^{10}$)—$NR^{12}$, —N=C($R^{11}$)—$NR^2$—C(O)—, —C($R^9R^{10}$)—C($R^9R^{10}$)—$NR^2$—S(O)$_2$—, —C($R^9R^{10}$)—C($R^9R^{10}$)—S(O)$_2$—$NR^2$—, —C($R^9R^{10}$)—C($R^9R^{10}$)—C(O)—O—, —C($R^9R^{10}$)—S(O)$_2$—C($R^9R^{10}$)—, —C($R^9R^{10}$)—C($R^9R^{10}$)—S(O)$_2$—; —O—C($R^9R^{10}$)—C($R^9R^{10}$)—, —C($R^9R^{10}$)—C($R^9R^{10}$)—O—, —C($R^9R^{10}$)—C(O)—C($R^9R^{10}$)—, —C(O)—C($R^9R^{10}$)—C($R^9R^{10}$)— and —C($R^9R^{10}$)—$NR^2$—S(O)$_2$—$NR^2$—;

Q is a covalent bond or $CH_2$;

W is CH or N;

X is $CR^9R^{10}$, C=$CH_2$ or C=O;

Y is $CR^9R^{10}$, O or $NR^2$;

Z is C=O, C=S or S(O)$_2$;

$G^1$ is hydrogen, halo, hydroxy, nitro, amino, cyano, phenyl, carboxyl, —$CONH_2$, —($C_1$-$C_4$)alkyl optionally independently substituted with one or more phenyl, one or more halogens or one or more hydroxy groups, —($C_1$-$C_4$)alkoxy optionally independently substituted with one or more phenyl, one or more halogens or one or more hydroxy groups, —($C_1$-$C_4$)alkylthio, phenoxy, —COO($C_1$-$C_4$)alkyl; N, N-di-($C_1$-$C_4$)alkylamino, —($C_2$-$C_6$)alkenyl optionally independently substituted with one or more phenyl, one or more halogens or one or more hydroxy groups, —($C_2$-$C_6$)alkynyl optionally independently substituted with one or more phenyl, one or more halogens or one or more hydroxy groups, —($C_3$-$C_6$)cycloalkyl optionally independently substituted with one or more ($C_1$-$C_4$)alkyl groups, one or more halogens or one or more hydroxy groups, —($C_1$-$C_4$)alkylamino carbonyl or di-($C_1$-$C_4$) alkylamino carbonyl; $G^2$ and $G^3$ are each independently selected from the group consisting of hydrogen, halo, hydroxy, —($C_1$-$C_4$)alkyl optionally independently substituted with one to three halo groups and —($C_1$-$C_4$)alkoxy optionally independently substituted with one to three halo groups;

$R^1$ is hydrogen, —CN, —$(CH_2)_qN(X^6)C(O)X^6$, —$(CH_2)_qN(X^6)C(O)(CH_2)_t$—$A^1$, —$(CH_2)_qN(X^6)S(O)_2(CH_2)_t$—$A^1$, —$(CH_2)_qN(X^6)S(O)_2X^6$, —$(CH_2)_qN(X^6)C(O)N(X^6)(CH_2)_t$—$A^1$, —$(CH_2)_qN(X^6)C(O)N(X^6)(X^6)$, —$(CH_2)_qC(O)N(X^6)(X^6)$, —$(CH_2)_qC(O)N(X^6)(CH_2)_t$—$A^1$, —$(CH_2)_qC(O)OX^6$, —$(CH_2)_qC(O)O(CH_2)_t$—$A^1$, —$(CH_2)_qOX^6$, —$(CH_2)_qOC(O)X^6$, —$(CH_2)_qOC(O)(CH_2)_t$—$A^1$, —$(CH_2)_qOC(O)N(X^6)(CH_2)_t$—$A^1$, —$(CH_2)_qOC(O)N(X^6)(X^6)$, —$(CH_2)_qC(O)X^6$, —$(CH_2)_qC(O)(CH_2)_t$—$A^1$, —$(CH_2)_qN(X^6)C(O)OX^6$, —$(CH_2)_qN(X^6)S(O)_2N(X^6)(X^6)$, —$(CH_2)_qS(O)_mX^6$, —$(CH_2)_qS(O)_m(CH_2)_t$—$A^1$, —($C_1$-$C_{10}$)alkyl, —$(CH_2)_t$—$A^1$, —$(CH_2)_q$—($C_3$-$C_7$)cycloalkyl, —$(CH_2)_q$—$Y^1$—($C_1$-$C_6$)alkyl, —$(CH_2)_q$—$Y^1$—$(CH_2)_t$—$A^1$ or —$(CH_2)_q$—$Y^1$—($C_3$-$C_7$)cycloalkyl;

where the alkyl and cycloalkyl groups in the definition of $R^1$ are optionally substituted with ($C_1$-$C_4$)alkyl, hydroxy, ($C_1$-$C_4$)alkoxy, carboxyl, —$CONH_2$, —$S(O)_m(C_1$-$C_6$)alkyl, —$CO_2(C_1$-$C_4$)alkyl ester, 1 H-tetrazol-5-yl or 1, 2 or 3 fluoro groups;

$Y^1$ is O, S(O)$_m$, —C(O)N$X^6$—, —CH=CH—, —C≡C—, —N($X^6$)C(O)—, —C(O)N$X^6$—, —C(O)O—, —OC(O)N($X^6$)— or —OC(O)—;

q is 0, 1, 2, 3 or 4;

t is 0, 1, 2 or 3;

said $(CH_2)_q$ group and $(CH_2)_t$ group in the definition of $R^1$ are optionally independently substituted with hydroxy, ($C_1$-$C_4$)alkoxy, carboxyl, —$CONH_2$, —$S(O)_m(C_1$-$C_6$)alkyl, —$CO_2(C_1$-$C_4$)alkyl ester, 1H-tetrazol-5-yl, 1, 2 or 3 fluoro groups or 1 or 2 ($C_1$-$C_4$)alkyl groups;

$R^{1A}$ is selected from the group consisting of hydrogen, F, Cl, Br, I, ($C_1$-$C_6$)alkyl, phenyl($C_1$-$C_3$)alkyl, pyridyl ($C_1$-$C_3$)alkyl, thiazolyl($C_1$-$C_3$)alkyl and thienyl ($C_1$-$C_3$)alkyl, provided that $R^{1A}$ is not F, Cl, Br or I when a heteroatom is vicinal to C";

$R^2$ is hydrogen, ($C_1$-$C_8$)alkyl, —($C_0$-$C_3$)alkyl-($C_3$-$C_8$) cycloalkyl, —($C_1$-$C_4$)alkyl-$A^1$ or $A^1$;

where the alkyl groups and the cycloalkyl groups in the definition of $R^2$ are optionally substituted with hydroxy, —C(O)O$X^6$, —C(O)N($X^6$)($X^6$), —N($X^6$) ($X^6$), —$S(O)_m(C_1$-$C_6$)alkyl, —C(O)$A^1$, —C(O) ($X^6$), $CF_3$, CN or 1, 2 or 3 independently selected halo groups;

$R^3$ is selected from the group consisting of $A^1$, ($C_1$-$C_{10}$) alkyl, —($C_1$-$C_6$)alkyl-$A^1$, —($C_1$-$C_6$)alkyl-($C_3$-$C_7$) cycloalkyl, —($C_1$-$C_5$)alkyl-$X^1$—($C_1$-$C_5$)alkyl, —($C_1$-$C_5$)alkyl-$X^1$—($C_0$-$C_5$)alkyl-$A^1$ and —($C_1$-$C_5$) alkyl-$X^1$—($C_1$-$C_5$)alkyl-($C_3$-$C_7$)cycloalkyl;

where the alkyl groups in the definition of $R^3$ are optionally substituted with —$S(O)_m(C_1$-$C_6$)alkyl, —C(O)O$X^3$, 1, 2, 3, 4 or 5 independently selected halo groups or 1, 2 or 3 independently selected —O$X^3$ groups;

$X^1$ is O, S(O)$_m$, —N($X^2$)C(O)—, —C(O)N($X^2$)—, —OC(O)—, —C(O)O—, —C$X^2$=C$X^2$—, —N($X^2$) C(O)O—, —OC(O)N($X^2$)— or —C≡C—;

$R^4$ is hydrogen, ($C_1$-$C_6$)alkyl or ($C_3$-$C_7$)cycloalkyl, or $R^4$ is taken together with $R^3$ and the carbon atom to which they are attached and form ($C_5$-$C_7$)cycloalkyl, ($C_5$-$C_7$) cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;

$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;

$R^6$ is a bond or is

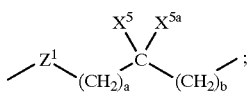

where a and b are each independently 0, 1, 2 or 3;

$X^5$ and $X^{5a}$ are each independently selected from the group consisting of hydrogen, $CF_3$, $A^1$ and optionally substituted $(C_1-C_6)$alkyl;

the optionally substituted $(C_1-C_6)$alkyl in the definition of $X^5$ and $X^{5a}$ is optionally substituted with a substituent selected from the group consisting of $A^1$, $OX^2$, —$S(O)_m(C_1-C_6)$alkyl, —$C(O)OX^2$, $(C_3-C_7)$cycloalkyl, —$N(X^2)(X^2)$ and —$C(O)N(X^2)(X^2)$;

or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then only one of $X^5$ or $X^{5a}$ is on the carbon atom and only one of $R^7$ or $R^8$ is on the nitrogen atom and further provided that when two alkylene bridges are formed then $X^5$ and $X^{5a}$ cannot be on the carbon atom and $R^7$ and $R^8$ cannot be on the nitrogen atom;

or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a bond, O or N—$X^2$, provided that when a and b are both 0 then $Z^1$ is not N—$X^2$ or O;

or $R^6$ is —$(CR^aR^b)_a$—E—$(CR^aR^b)_b$—, where the —$(CR^aR^b)_a$—group is attached to the carbonyl carbon of the amide group of the compound of formula I and the —$(CR^aR^b)_b$ group is attached to the terminal nitrogen atom of the compound of Formula I;

E is —O—, —S—, —CH=CH— or an aromatic moiety selected from

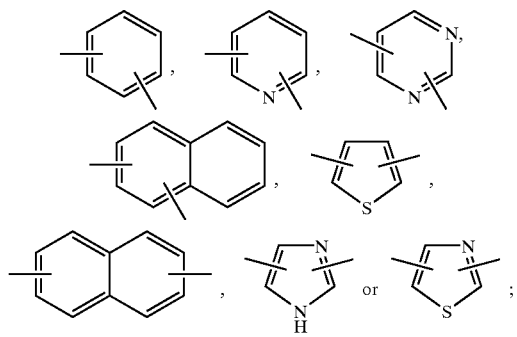

said aromatic moiety in the definition of E optionally substituted with up to three halo, hydroxy, —$N(R^c)(R^c)$, $(C_1-C_6)$alkyl or $(C_1-C_6)$alkoxy;

$R^a$ and $R^b$ are, for each occurrence, independently hydrogen, $(C_1-C_6)$alkyl, trifluoromethyl, phenyl or monosubstituted $(C_1-C_6)$alkyl where the substituents are imidazolyl, naphthyl, phenyl, indolyl, p-hydroxyphenyl, —$OR^c$, $S(O)_mR^c$, $C(O)OR^c$, $(C_3-C_7)$cycloalkyl, —$N(R^c)(R^c)$, —$C(O)N(R^c)(R^c)$, or $R^a$ or $R^b$ may independently be joined to one or both of $R^7$ or E (where E is other than O, S or —CH=CH—) to form an alkylene bridge between the terminal nitrogen and the alkyl portion of the $R^a$ or $R^b$ and the $R^7$ or E group, wherein the bridge contains 1 to 8 carbon atoms; or $R^a$ and $R^b$ may be joined to one another to form a $(C_3-C_7)$cycloalkyl;

$R^c$, for each occurrence, is independently hydrogen or $(C_1-C_6)$alkyl;

a and b are independently 0, 1, 2 or 3, with the proviso that if E is —O— or —S—, b is other than 0 or 1 and with the further proviso that if E is —CH=CH—, b is other than 0;

$R^7$ and $R^8$ are each independently hydrogen or optionally substituted $(C_1-C_6)$alkyl;

where the optionally substituted $(C_1-C_6)$alkyl in the definition of $R^7$ and $R^8$ is optionally independently substituted with $A^1$, —$C(O)O$—$(C_1-C_6)$alkyl, —$S(O)_m(C_1-C_6)$alkyl, 1 to 5 halo groups, 1 to 3 hydroxy groups, 1 to 3 —O—$C(O)(C_1-C_{10})$alkyl groups or 1 to 3 $(C_1-C_6)$alkoxy groups; or $R^7$ and $R^8$ can be taken together to form —$(CH_2)_r$—L—$(CH_2)_r$—;

where L is $C(X^2)(X^2)$, $S(O)_m$ or $N(X^2)$;

$R^9$ and $R^{10}$ are each independently selected from the group consisting of hydrogen, fluoro, hydroxy and $(C_1-C_5)$alkyl optionally independently substituted with 1–5 halo groups;

$R^{11}$ is selected from the group consisting of $(C_1-C_5)$alkyl and phenyl optionally substituted with 1–3 substituents each independently selected from the group consisting of $(C_1-C_5)$alkyl, halo and $(C_1-C_5)$alkoxy;

$R^{12}$ is selected from the group consisting of $(C_1-C_5)$alkylsulfonyl, $(C_1-C_5)$alkanoyl and $(C_1-C_5)$alkyl where the alkyl portion is optionally independently substituted by 1–5 halo groups;

$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —$C(O)N(X^6)(X^6)$, —$C(O)OX^6$, oxo, $(C_1-C_6)$alkyl, nitro, cyano, benzyl, —$S(O)_m(C_1-C_6)$alkyl, 1 H-tetrazol-5-yl, phenyl, phenylalkyloxy, halophenyl, methylenedioxy, —$N(X^6)(X^6)$, —$N(X^6)C(O)(X^6)$, —$S(O)_2N(X^6)(X^6)$, —$N(X^6)S(O)_2$-phenyl, —$N(X^6)S(O)_2X^6$, —$CONX^{11}X^{12}$, —$S(O)_2NX^{11}X^{12}$, —$NX^6S(O)_2X^{12}$, —$NX^6CONX^{11}X^{12}$, —$NX^6S(O)_2NX^{11}X^{12}$, —$NX^6C(O)X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1-C_6)$alkyl; the optionally substituted $(C_1-C_6)$alkyl defined for $X^{11}$ is optionally independently substituted with phenyl, phenoxy, $(C_1-C_6)$alkoxycarbonyl, —$S(O)_m(C_1-C_6)$alkyl, 1 to 5 halo groups, 1 to 3 hydroxy groups, 1 to 3 $(C_1-C_{10})$alkanoyloxy groups or 1 to 3 $(C_1-C_6)$alkoxy groups;

$X^{12}$ is hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;

or $X^{11}$ and $X^{12}$ are taken together to form —$(CH_2)_r$—$L^1$—$(CH_2)_r$—;

$L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with —$S(O)_m(C_1-C_6)$alkyl, —$C(O)OX^3$, 1 to 5 halo groups or 1–3 $OX^3$ groups;

$X^3$ for each occurrence is independently hydrogen or $(C_1-C_6)$alkyl;

$X^6$ for each occurrence is independently hydrogen, optionally substituted $(C_1-C_6)$alkyl, $(C_2-C_6)$ halogenated alkyl, optionally substituted $(C_3-C_7)$ cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, $CONH_2$, —$S(O)_m(C_1-C_6)$alkyl, carboxylate $(C_1-C_4)$ alkyl ester or 1 H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$ as a ring member;

$X^7$ is hydrogen or $(C_1-C_6)$alkyl optionally substituted with hydroxy;

m for each occurrence is independently 0, 1 or 2;

with the provisos that:
1) $X^6$ and $X^{12}$ cannot be hydrogen when attached to $C(O)$ or $S(O)_2$ in the form $C(O)X^6$, $C(O)X^{12}$, $S(O)_2X^6$ or $S(O)_2X^{12}$; and
2) when $R^6$ is a bond then L is $N(X^2)$ and each r in the definition —$(CH_2)_r$—L—$(CH_2)_r$— is independently 2 or 3.

More preferably, the present invention provides such method wherein the compound is of the structural formula below, which is designated herein as Formula I-A

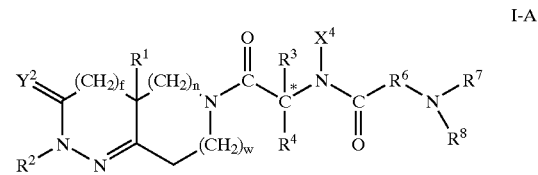

a racemic-diastereomeric mixture or an optical isomer of said compound or a pharmaceutically-acceptable salt or prodrug thereof, or a tautomer thereof, wherein f is 0;

n is 0 and w is 2, or n is 1 and w is 1, or n is 2 and w is 0;

Y is oxygen or sulfur;

$R^1$ is hydrogen, —CN, —$(CH_2)_qN(X^6)C(O)X^6$, —$(CH_2)_q N(X^6)C(O)(CH_2)_t-A^1$, —$(CH_2)_qN(X^6)SO_2(CH_2)_t-A^1$, —$(CH_2)_qN(X^6)SO_2X^6$, —$(CH_2)_qN(X^6)C(O)N(X^6)(CH_2)_t-A^1$, —$(CH_2)_qN(X^6)C(O)N(X^6)(X^6)$, —$(CH_2)_q C(O)N(X^6)(X^6)$, —$(CH_2)_qC(O)N(X^6)(CH_2)_t-A^1$, —$(CH_2)_qC(O)OX^6$, —$(CH_2)_qC(O)O(CH_2)_t-A^1$, —$(CH_2)_qOX^6$, —$(CH_2)_qOC(O)X^6$, —$(CH_2)_qOC(O)(CH_2)_t-A^1$, —$(CH_2)_qOC(O)N(X^6)(CH_2)_t-A^1$, —$(CH_2)_qOC(O)N(X^6)(X^6)$, —$(CH_2)_qC(O)X^6$, —$(CH_2)_qC(O)(CH_2)_t-A^1$, —$(CH_2)_qN(X^6)C(O)OX^6$, —$(CH_2)_qN(X^6)SO_2N(X^6)(X^6)$, —$(CH_2)_qS(O)_mX^6$, —$(CH_2)_qS(O)_m(CH_2)_t-A^1$, —$(C_1-C_{10})$alkyl, —$(CH_2)_t-A^1$, —$(CH_2)_q-(C_3-C_7)$cycloalkyl, —$(CH_2)_q-Y^1-(C_1-C_6)$alkyl, —$(CH_2)_q-Y^1-(CH_2)_t-A^1$ or —$(CH_2)_q-Y^1-(CH_2)_t-(C_3-C_7)$cycloalkyl;

where the alkyl and cycloalkyl groups in the definition of $R^1$ are optionally substituted with $(C_1-C_4)$alkyl, hydroxyl, $(C_1-C_4)$alkoxy, carboxyl, —$CONH_2$, —$S(O)_m(C_1-C_6)$alkyl, —$CO_2(C_1-C_4)$alkyl ester, 1 H-tetrazol-5-yl or 1, 2 or 3 fluoro;

$Y^1$ is O, $S(O)_m$, —$C(O)NX^6$—, —CH=CH—, —C≡C—, —$N(X^6)C(O)$—, —$C(O)O$—, —$OC(O)N(X^6)$— or —$OC(O)$—;

q is 0, 1, 2, 3 or 4;

t is 0, 1, 2 or 3;

said $(CH_2)_q$ group and $(CH_2)_t$ group may each be optionally substituted with hydroxyl, $(C_1-C_4)$ alkoxy, carboxyl, —$CONH_2$, —$S(O)_m(C_1-C_6)$alkyl, —$CO_2(C_1-C_4)$alkyl ester, 1H-tetrazol-5-yl, 1, 2 or 3 fluoro, or 1 or 2 $(C_1-C_4)$alkyl;

$R^2$ is hydrogen, $(C_1-C_8)$alkyl, —$(C_0-C_3)$alkyl-$(C_3-C_8)$ cycloalkyl, —$(C_1-C_4)$alkyl-$A^1$ or $A^1$;

where the alkyl groups and the cycloalkyl groups in the definition of $R^2$ are optionally substituted with hydroxyl, —C(O)OX⁶, —C(O)N(X⁶)(X⁶), —N(X⁶)(X⁶), —S(O)$_m$(C₁–C₆)alkyl, —C(O)A¹, —C(O)(X⁶), CF₃, CN or 1, 2 or 3 halogen;

R³ is A¹, (C₁–C₁₀)alkyl, —(C₁–C₈)alkyl-A¹, —(C₁–C₆)alkyl-(C₃–C₇)cycloalkyl, —(C₁–C₅)alkyl-X¹-(C₁–C₅)alkyl, —(C₁–C₅)alkyl-X¹—(C₀–C₅)alkyl-A¹ or —(C₁–C₅)alkyl-X¹—(C₁–C₅)alkyl-(C₃–C₇)cycloalkyl;

where the alkyl groups in the definition of R³ are optionally substituted with, —S(O)$_m$(C₁–C₆)alkyl, —C(O)OX³, 1, 2, 3, 4 or 5 halogens, or 1, 2 or 3 OX³;

X¹ is O, S(O)$_m$, —N(X²)C(O)—, —C(O)N(X²)—, —OC(O)—, —C(O)O—, —CX²=CX²—, —N(X²)C(O)O—, —OC(O)N(X²)— or —C≡C—;

R⁴ is hydrogen, (C₁–C₆)alkyl or (C₃–C₇)cycloalkyl;

X⁴ is hydrogen or (C₁–C₆)alkyl or X⁴ is taken together with R⁴ and the nitrogen atom to which X⁴ is attached and the carbon atom to which R⁴ is attached and form a five to seven membered ring;

R⁶ is a bond or is

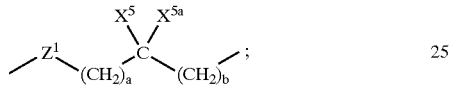

where a and b are independently 0, 1, 2 or 3;

X⁵ and X⁵ᵃ are each independently selected from the group consisting of hydrogen, trifluoromethyl, A¹ and optionally substituted (C₁–C₆)alkyl;

the optionally substituted (C₁–C₆)alkyl in the definition of X⁵ and X⁵ᵃ is optionally substituted with a substituent selected from the group consisting of A¹, OX², —S(O)$_m$(C₁–C₆)alkyl, —C(O)OX², (C₃–C₇)cycloalkyl, —N(X²)(X²) and —C(O)N(X²)(X²);

R⁷ and R⁸ are independently hydrogen or optionally substituted (C₁–C₆)alkyl;

where the optionally substituted (C₁–C₆)alkyl in the definition of R⁷ and R⁸ is optionally independently substituted with A¹, —C(O)O—(C₁–C₆)alkyl, —S(O)$_m$(C₁–C₆)alkyl, 1 to 5 halogens, 1 to 3 hydroxy, 1 to 3 —O—C(O)(C₁–C₁₀)alkyl or 1 to 3 (C₁–C₆)alkoxy; or R⁷ and R⁸ can be taken together to form —(CH₂)$_r$—L—(CH₂)$_r$—;

where L is C(X²)(X²), S(O)$_m$ or N(X²);

A¹ in the definition of R¹ is a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

A¹ in the definition of R², R³, R⁶, R⁷ and R⁸ is independently (C₅–C₇)cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

A¹ for each occurrence is independently optionally substituted, in one or optionally both rings if A¹ is a bicyclic ring system, with up to three substituents, each substituent independently selected from the group consisting of F, Cl, Br, I, OCF₃, OCF₂H, CF₃, CH₃, OCH₃, —OX⁶, —C(O)N(X⁶)(X⁶), —C(O)OX⁶, oxo, (C₁–C₆)alkyl, nitro, cyano, benzyl, —S(O)$_m$(C₁–C₆)alkyl, 1 H-tetrazol-5-yl, phenyl, phenoxy, phenylalkyloxy, halophenyl, methylenedioxy, —N(X⁶)(X⁶), —N(X⁶)C(O)(X⁶), —SO₂N(X⁶)(X⁶), —N(X⁶)SO₂-phenyl, —N(X⁶)SO₂X⁶, —CONX¹¹X¹², —SO₂NX¹¹X¹², —NX⁶SO₂X¹², —NX⁶CONX¹¹X¹², —NX⁶SO₂NX¹¹X¹², —NX⁶C(O)X¹², imidazolyl, thiazolyl or tetrazolyl, provided that if Al is optionally substituted with methylenedioxy then it can only be substituted with one methylenedioxy;

where X¹¹ is hydrogen or optionally substituted (C₁–C₆)alkyl;

the optionally substituted (C₁–C₆)alkyl defined for X¹¹ is optionally independently substituted with phenyl, phenoxy, (C₁–C₆)alkoxycarbonyl, —S(O)$_m$(C₁–C₆)alkyl 1 to 5 halogens, 1 to 3 hydroxy, 1 to 3 (C₁–C₁₀)alkanoyloxy or 1 to 3 (C₁–C₆)alkoxy;

X¹² is hydrogen, (C₁–C₆)alkyl, phenyl, thiazolyl, imidazolyl, furyl or thienyl, provided that when X¹² is not hydrogen, X¹² is optionally substituted with one to three substituents independently selected from the group consisting of Cl, F, CH₃, OCH₃, OCF₃ and CF₃;

or X¹¹ and X¹² are taken together to form —(CH₂)$_r$—L¹—(CH₂)$_r$—;

where L¹ is C(X²)(X²), O, S(O)$_m$ or N(X²);

r for each occurrence is independently 1, 2 or 3;

X² for each occurrence is independently hydrogen, optionally substituted (C₁–C₆)alkyl, or optionally substituted (C₃–C₇)cycloalkyl, where the optionally substituted (C₁–C₆)alkyl and optionally substituted (C₃–C₇)cycloalkyl in the definition of X² are optionally independently substituted with —S(O)$_m$(C₁–C₆)alkyl, —C(O)OX³, 1 to 5 halogens or 1–3 OX³;

X³ for each occurrence is independently hydrogen or (C₁–C₆)alkyl;

X⁶ is independently hydrogen, optionally substituted (C₁–C₆)alkyl, (C₂–C₆)halogenated alkyl, optionally substituted (C₃–C₇)cycloalkyl, (C₃–C₇)-halogenatedcycloalkyl, where optionally substituted (C₁–C₆)alkyl and optionally substituted (C₃–C₇)cycloalkyl in the definition of X⁶ is optionally independently substituted by 1 or 2 (C₁–C₄)alkyl, hydroxyl, (C₁–C₄)alkoxy, carboxyl, CONH₂, —S(O)$_m$(C₁–C₆)alkyl, carboxylate (C₁–C₄)alkyl ester, or 1H-tetrazol-5-yl; or when there are two X⁶ groups on one atom and both X⁶ are independently (C₁–C₆)alkyl, the two (C¹–C₆)alkyl groups may be optionally joined and, together with the atom to which the two X⁶ groups are attached, form a 4- to 9-membered ring optionally having oxygen, sulfur or NX⁷;

$X^7$ is hydrogen or $(C_1-C_6)$alkyl optionally substituted with hydroxyl; and m for each occurrence is independently 0, 1 or 2;

with the proviso that:

$X^6$ and $X^{12}$ cannot be hydrogen when it is attached to C(O) or $SO_2$ in the form $C(O)X^6$, $C(O)X^{12}$, $SO_2X^6$ or $SO_2X^{12}$; and when $R^6$ is a bond then L is $N(X^2)$ and each r in the definition —$(CH_2)_r$—L—$(CH_2)_r$— is independently 2 or 3.

More preferably, the present invention provides such method wherein the compound is 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug thereof or a pharmaceutically acceptable salt of the compound or the prodrug. Even more preferably, the present invention provides such method wherein the compound is 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide, L-tartrate.

Also, more preferably, the present invention provides such method wherein the compound is 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide, a prodrug thereof or a pharmaceutically acceptable salt of the compound or the prodrug. Even more preferably, the present invention provides such method wherein the compound is the (L)-(+)-tartaric acid salt of 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide.

Also, more preferably, the present invention provides such method wherein the compound is 2-amino-N-(1(R)-benzyloxymethyl-2-(1,3-dioxo-8a(S)-pyridin-2-ylmethyl-2-(2,2,2-trifluoro-ethyl)-hexahydro-imidazo[1,5-a]pyrazin-7-yl)-2-oxo-ethyl)-2-methyl-propionamide, a prodrug thereof or a pharmaceutically acceptable salt of the compound or the prodrug. Even more preferably, the present invention provides such method wherein the compound is the (L)-(+)-tartaric acid salt of 2-amino-N-(1 (R)-benzyloxymethyl-2-(1,3-dioxo-8a(S)-pyridin-2-ylmethyl-2-(2,2,2-trifluoro-ethyl)-hexahydro-imidazo[1,5-a]pyrazin-7-yl)-2-oxo-ethyl)-2-methyl-propionamide.

The present invention provides such method which further comprises administering a prokinetic agent. More particularly, the present invention provides such method wherein the prokinetic agent is selected from the group consisting of cisapride monohydrate, metoclopramide, erythromycin, domperidone, ondansetron, tropisetron, mosapride and itopride.

The present invention provides such method which further comprises administering a recombinant growth hormone or a growth hormone secretagogue selected from the group consisting of GHRP-6, GHRP-1, GHRP-2, growth hormone releasing factor, an analog of growth hormone releasing factor, IGF-I and IGF-II.

In addition, the present invention provides a method of stimulating gastrointestinal transit in a patient which comprises administering to the patient a gastrointestinal transit stimulating effective amount of a growth hormone secretagogue.

More particularly, the present invention provides such method wherein the growth hormone secretagogue is an orally active growth hormone secretagogue. Even more particularly, the present invention provides such method wherein the growth hormone secretagogue is orally administered.

More particularly, the present invention provides such method wherein the growth hormone secretagogue is a non-peptidyl growth hormone secretagogue.

More particularly, the present invention provides such method wherein the patient is a human.

The present invention provides a method of stimulating gastrointestinal transit in a patient which comprises administering to the patient a gastrointestinal transit stimulating effective amount of a compound of the Formula I, wherein the variables are as defined above. More preferably, the present invention provides such method wherein the compound is of the Formula I-A wherein the variables are as defined above.

Even more preferably, the present invention provides such method wherein the compound is selected from the following: 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug thereof or a pharmaceutically acceptable salt of said compound or said prodrug; 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide, L-tartrate; 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3c]-pyridin-5-yl)-ethyl)-2-methyl-propionamide, a prodrug thereof or a pharmaceutically acceptable salt of said compound or said prodrug; the (L)-(+)-tartaric acid salt of 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide; 2-amino-N-{1(R)-benzyloxymethyl-2-[1,3-dioxo-8a(S)-pyridin-2-yl methyl-2-(2,2,2-trifluoro-ethyl)-hexahydro-imidazo[1,5-a]pyrazin-7-yl]-2-oxo-ethyl}-2-methyl-propionamide, a prodrug thereof or a pharmaceutically acceptable salt of said compound or said prodrug; and the (L)-(+)-tartaric acid salt of 2-amino-N-(1 (R)-benzyloxymethyl-2-(1,3-dioxo-8a(S)-pyridin-2-ylmethyl-2-(2,2,2-trifluoro-ethyl)-hexahydro-imidazo[1,5-a]pyrazin-7-yl)-2-oxo-ethyl)-2-methyl-propionamide.

The present invention provides such method which further comprises administering a prokinetic agent. More particularly, the present invention provides such method wherein the prokinetic agent is selected from the group consisting of cisapride monohydrate, metoclopramide, erythromycin, domperidone, ondansetron, tropisetron, mosapride and itopride.

The present invention provides such method which further comprises administering a recombinant growth hormone or a growth hormone secretagogue selected from the group consisting of GHRP-6, GHRP-1, GHRP-2, growth hormone releasing factor, an analog of growth hormone releasing factor, IGF-I and IGF-II.

In addition, the present invention provides a method for treating a condition selected from the group consisting of gastroesophageal reflux disease, gastroparesis, postoperative ileus, emesis, constipation and colonic pseudo-obstruction in a patient which comprises administering to the patient a condition treating effective amount of a growth hormone secretagogue. More particularly, the present invention provides such method wherein the condition is gastroesophageal reflux disease, gastroparesis, postoperative ileus or emesis.

More particularly, the present invention provides such method wherein the growth hormone secretagogue is an orally active growth hormone secretagogue. Even more particularly, the present invention provides such method wherein the growth hormone secretagogue is orally administered.

More particularly, the present invention provides such method wherein the growth hormone secretagogue is a non-peptidyl growth hormone secretagogue.

More particularly, the present invention provides such method wherein the patient is a human.

The present invention provides a method for treating a condition selected from the group consisting of gastroesophageal reflux disease, gastroparesis, postoperative ileus, emesis, constipation and colonic pseudo-obstruction in a patient which comprises administering to the patient a condition treating effective amount of a compound of the Formula I, wherein the variables are as defined above. More preferably, the present invention provides such method wherein the compound is of the Formula I-A.

Even more preferably, the present invention provides such method wherein the compound is selected from the following: 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug thereof or a pharmaceutically acceptable salt of said compound or said prodrug; 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide, L-tartrate; 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide, a prodrug thereof or a pharmaceutically acceptable salt of said compound or said prodrug; the (L)-(+)-tartaric acid salt of 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide; 2-amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, a prodrug thereof or a pharmaceutically acceptable salt of said compound or said prodrug; and the (L)-(+)-tartaric acid salt of 2-amino-N-(1(R)-benzyloxymethyl-2-(1,3-dioxo-8a(S)-pyridin-2-ylmethyl-2-(2,2,2-trifluoro-ethyl)-hexahydro-imidazo[1,5-a]pyrazin-7-yl)-2-oxo-ethyl)-2-methyl-propionamide.

The present invention provides such method which further comprises administering a prokinetic agent. More particularly, the present invention provides such method wherein the prokinetic agent is selected from the group consisting of cisapride monohydrate, metoclopramide, erythromycin, domperidone, ondansetron, tropisetron, mosapride and itopride.

The present invention provides such method which further comprises administering a recombinant growth hormone or a growth hormone secretagogue selected from the group consisting of GHRP-6, GHRP-1, GHRP-2, growth hormone releasing factor, an analog of growth hormone releasing factor, IGF-I and IGF-II.

The present invention provides a pharmaceutical composition comprising a compound of Formula I, an isomer thereof, a prodrug of said compound or isomer, or a pharmaceutically acceptable salt of said compound, isomer or prodrug, or a tautomer thereof, as defined above; and an additional compound useful to treat a condition selected from the group consisting of gastroesophageal reflux disease, gastroparesis, postoperative ileus, emesis, constipation and colonic pseudo-obstruction. More particularly, the present invention provides such composition wherein the condition is gastroesophageal reflux disease, gastroparesis, postoperative ileus or emesis.

The present invention provides such composition wherein the additional compound is a prokinetic agent. More particularly, the present invention provides such composition wherein the prokinetic agent is selected from the group consisting of cisapride monohydrate, metoclopramide, erythromycin, domperidone, ondansetron, tropisetron, mosapride and itopride.

Finally, the present invention provides a kit for treating a condition selected from the group consisting of gastroesophageal reflux disease, gastroparesis, postoperative ileus, emesis, constipation and colonic pseudo-obstruction, the kit comprising:

a) a first pharmaceutical composition comprising a compound of Formula I, an isomer thereof, a prodrug of said compound or isomer, a pharmaceutically acceptable salt of said compound, isomer or prodrug, or a tautomer thereof, as defined above;

b) a second pharmaceutical composition comprising an additional compound useful for treating a condition selected from the group consisting of gastroesophageal reflux disease, gastroparesis, postoperative ileus, emesis, constipation and colonic pseudo-obstruction; and c) a container.

DETAILED DESCRIPTION OF THE INVENTION

The present invention is directed to a method for stimulating the motility of the gastrointestinal system. In particular, the present invention provides a method for stimulating the motility of the gastrointestinal system comprising the administration of a growth hormone secretagogue. More particularly, the present invention provides a method for stimulating the motility of the gastrointestinal system comprising the administration of a compound of Formula I.

In view of their ability-to stimulate gastrointestinal (GI) motility, the compounds of the present invention may be useful to normalize or improve the gastric and/or intestinal transit and/or emptying in subjects suffering from a decreased peristalsis of the stomach and/or the small and/or large intestines, especially the stomach and the small intestines. Therefore, the compounds of the present invention may be useful to treat diseases of impaired GI motility such as gastroesophageal reflux disease, gastroparesis (e.g., diabetic and postsurgical), emesis (e.g., that caused by cancer chemotherapy agents), postoperative ileus, constipation (e.g., that associated with the hypomotility phase of irritable bowel syndrome) and colonic pseudo-obstruction. The compounds of the present invention may be especially useful to treat diseases such as gastroesophageal reflux disease, gastroparesis, emesis and postoperative ileus.

In the present invention, it is preferred that the patient is a human and is applicable to both old and young people.

By the term "growth hormone secretagogue" is meant any exogenously administered compound or agent that directly or indirectly stimulates or increases the endogenous release of growth hormone, growth hormone-releasing hormone or somatostatin in an animal, in particular, a human. The growth hormone secretagogue may be peptidyl or non-peptidyl in nature, however, the use of an orally active growth hormone secretagogue is preferred. In addition, it is preferred that the growth hormone secretagogue induce or amplify a pulsatile release of endogenous growth hormone.

The expression "prodrug" refers to compounds that are drug precursors which, following administration, release the drug in vivo via some chemical or physiological process (e.g., a prodrug on being brought to the physiological pH is converted to the desired drug form). A prodrug of the compound of Formula I may be used in the present invention. Exemplary prodrugs are disclosed in the art, particularly in the references cited herein and incorporated herein by reference.

The compound useful in the present invention may be used alone or in combination with one or more growth hormone secretagogues or with one or more agents which are known to be beneficial for impaired GI motility. The compounds useful in the present invention and the other agent may be coadministered, either in concomitant therapy or in a fixed combination. For example, the compound may be administered in combination with other compounds-which are known in the art to be prokinetic agents.

Representative growth hormone secretagogues are disclosed in the following International Patent Applications (listed by Publication Nos.), issued U.S. patents and published European patent applications, which are incorporated herein by reference, WO 98/46569, WO 98/51687, WO 98/58947, WO 98/58949, WO 98/58950, WO 99/08697, WO 99/09991, WO 95/13069, U.S. Pat. Nos. 5,492,916, 5,494,919, WO 95/14666, WO 94/19367, WO 94/13696, WO 94/11012, U.S. Pat. No. 5,726,319, WO 95/11029, WO 95/17422, WO 95/17423, WO 95/34311, WO 96/02530, WO 96/22996, WO 96/22997, WO 96/24580, WO 96/24587, U.S. Pat. No. 5,559,128, WO 96/32943, WO 96/33189, WO 96/15148, WO 96/38471, WO 96/35713, WO 97/00894, WO 97/07117, WO 97/06803, WO 97/11697, WO 97/15573, WO 97/22367, WO 97/23508, WO 97/22620, WO 97/22004, WO 97/21730, WO 97/24369, U.S. Pat. No. 5,663,171, WO 97/34604, WO 97/36873, WO 97/40071, WO 97/40023, WO 97/41878, WO 97/41879, WO 97/46252, WO 97/44042. WO 97/38709, WO 98/03473, WO 97/43278, U.S. Pat. Nos. 5,721,251, 5,721,250, WO 98/10653, U.S. Pat. Nos. 5,919, 777, 5,830,433 and EP 0995748.

A representative first group of growth hormone secretagogues is set forth in International Patent Application, Publication No. WO 97/24369, which is incorporated herein by reference, as compounds having the structural formula below, which is designated herein as Formula II:

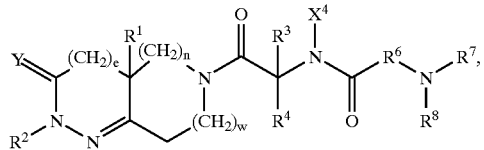

wherein the various substituents are as defined in WO 97/24369. Said compounds are prepared as disclosed therein.

2-Amino-N-(2-(3a-(R)-benzyl-2-methyl-3-oxo-2,3,3a,4, 6,7-hexahydro-pyrazolo-[4,3-c]pyridin-5-yl)-1-(R)-benzyloxymethyl-2-oxo-ethyl)-isobutyramide, having the following structure:

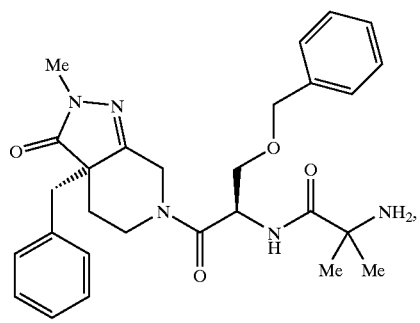

and 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c] pyridin-5-yl)-ethyl)-2-methyl-propionamide, having the following structure:

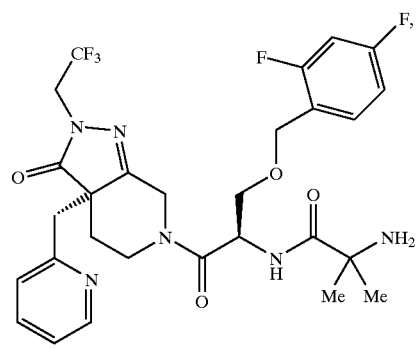

and the pharmaceutically acceptable salts thereof are within the scope of the disclosure of International Patent Application, Publication Number WO 97/24369.

A representative second group of growth hormone secretagogues is set forth in International Patent Application, Publication No. WO 98/58947, which is incorporated by reference herein, as compounds having the structural formula below, which is designated herein as Formula III:

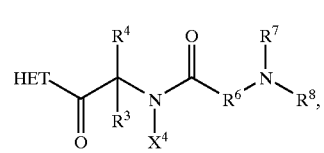

wherein the various substituents are as defined in WO 98/58947. Said compounds are prepared as disclosed therein or as described herein.

The most preferred compound within this second group which may be employed in the present invention is identified as having the following name and structure: 2-amino-N-(1 (R)-benzyloxymethyl-2-(1,3-dioxo-8a(S)-pyridin-2-ylmethyl-2-(2,2,2-trifluoro-ethyl)-hexahydro-imidazo[1,5-a]pyrazin-7-yl)-2-oxo-ethyl)-2-methyl-propionamide,

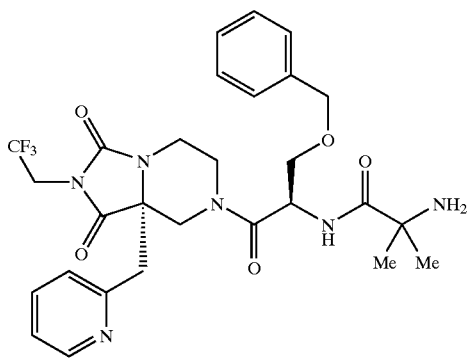

This compound is within the scope of the disclosure of International Patent Application, Publication No. WO 98/58947, and may be prepared as described in Examples Five and Six therein.

A representative third group of growth hormone secretagogues is set forth in Published European patent application 0995748, which is hereby incorporated by reference herein, which discloses certain dipeptide growth hormone secretagogues of the structural formula above, which is designated herein as Formula III, and their use for the treatment or prevention of musculoskeletal fraility including osteoporosis.

A representative fourth group of growth hormone secretagogues is set forth in U.S. Pat. No. 5,206,235, which is incorporated herein by reference, as having the following structure:

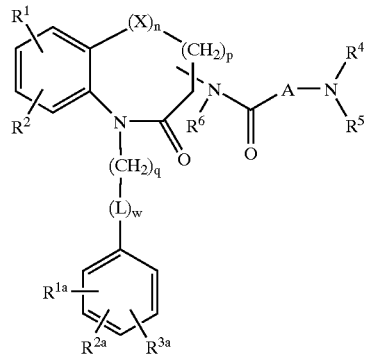

wherein the various substituents are as defined in U.S. Pat. No. 5,206,235. Said compounds are prepared as disclosed therein.

The most preferred compounds within this fourth group are identified as having the following structures:

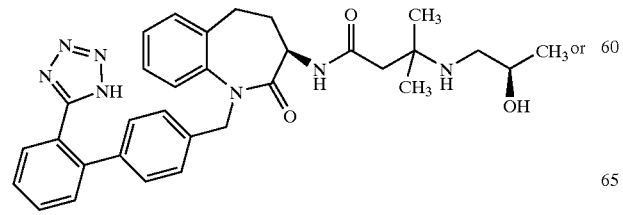

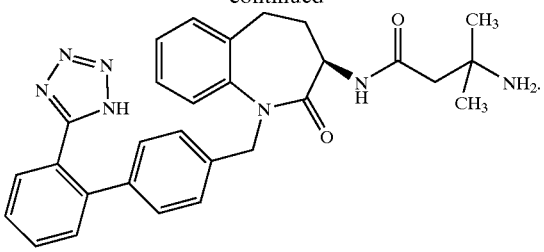

A representative fifth group of growth hormone secretagogues is set forth in U.S. Pat. No. 5,283,241, which is incorporated herein by reference, as having the following structural formula:

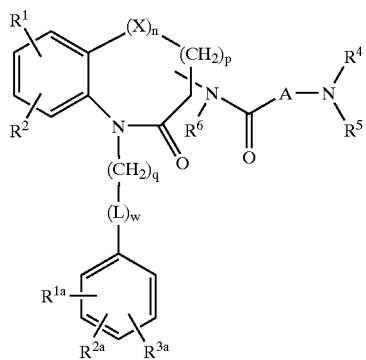

wherein the various substituents are as defined in U.S. Pat. No. 5,283,241. Said compounds are prepared as disclosed therein.

A representative sixth group of growth hormone secretagogues is disclosed in International Patent Application, Publication No. WO 97/41879, which is incorporated herein by reference, as compounds having the following structural formulas:

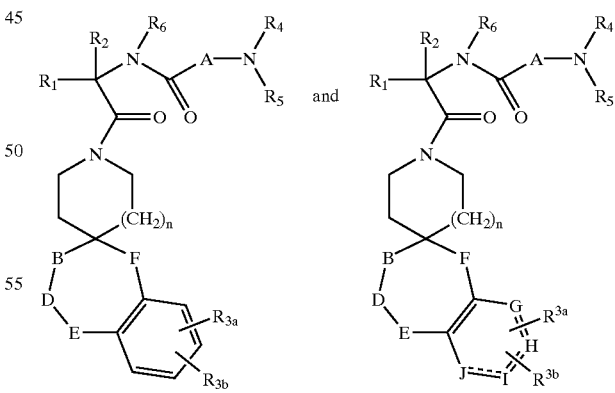

wherein the various substituents are as defined in WO97/41879. Said compounds are prepared as disclosed therein.

The most preferred compounds within this sixth group which may be employed in the present invention are identified as having the following structure:

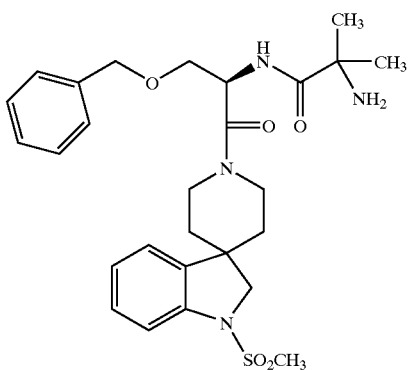

and pharmaceutically acceptable salts thereof, in particular, the methanesulfonate salt.

A representative seventh group of growth hormone secretagogues is disclosed in U.S. Pat. No. 5,492,916, which is incorporated herein by reference, as being compounds of the following structural formula:

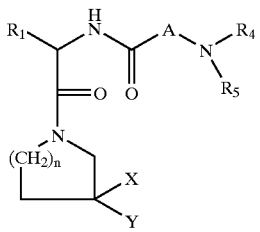

wherein the various substituents are as defined in U.S. Pat. No. 5,492,916. Said compounds are prepared as disclosed therein.

All of the compounds identified above may be prepared by procedures disclosed in the cited publications. Full descriptions of the preparation of the compounds which may be employed in the present invention may be found in the art, particularly in the references cited herein, which are incorporated herein by reference.

The compounds of Formula I used in the methods of the present invention all have at least one asymmetric center as noted, e.g., by the asterisk in the structural Formula I-B below. Additional asymmetric centers may be present in the compounds of Formula I depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the methods and combinations of the instant invention. In the case of the asymmetric center represented by the asterisk, it has been found that the absolute stereochemistry of the more active and thus more preferred isomer is shown in Formula I-B below:

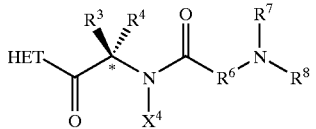

With the $R^4$ substituent as hydrogen, the spatial configuration of the asymmetric center corresponds to that in a D-amino acid. In most cases this is also designated an R-configuration although this will vary according to the values of $R^3$ and $R^4$ used in making R- or S-stereochemical assignments.

Certain compounds within the scope of the present invention may have the potential to exist in different tautomeric forms. All tautomers of a compound of the present invention are within the scope of the present invention. Also, for example, all keto-enol or imine-enamine forms of the compounds are included in the present invention. Those skilled in the art will recognize that the compound names contained herein may be based on a particular tautomer of a compound. While the name for only a particular tautomer may be used, it is intended that all tautomers are encompassed by the name of the particular tautomer and all tautomers are considered part of the present invention.

A compound within the scope of the present invention may exist in unsolvated as well as solvated forms with pharmaceutically acceptable solvents such as water, ethanol, and the like. The present invention contemplates and encompasses both the solvated and unsolvated forms.

Also included within the scope of the present invention are isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in compound and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

Full descriptions of preparation of the compounds employed in the present invention may be found, for example, in the following International Patent Applications (listed by Publication Nos.), issued U.S. patents and published European patent applications, which are incorporated herein by reference, WO 98/46569, WO 98/51687, WO 98/58947, WO 98/58949, WO 98/58950, WO 99/08697, WO 99/09991, WO 95/13069, U.S. Pat. Nos. 5,492,916, 5,494,919, WO 95/14666, WO 94/19367, WO 94/13696, WO 94/11012, U.S. Pat. No. 5,726,319, WO 95/11029, WO 95/17422, WO 95/17423, WO 95/34311, WO 96/02530, WO 96/22996, WO 96/22997, WO 96/24580, WO 96/24587, U.S. Pat. No. 5,559,128, WO 96/32943, WO 96/33189, WO 96/15148, WO 96/38471, WO 96/35713, WO 97/00894, WO 97/07117, WO 97/06803, WO 97/11697, WO 97/15573, WO 97/22367, WO 97/23508, WO 97/22620, WO 97/22004, WO 97/21730, WO 97/24369, U.S. Pat. No. 5,663,171, WO 97/34604, WO 97/36873, WO 97/40071, WO 97/40023, WO 97/41878, W097/41879, WO 97/46252, WO 97/44042, WO 97/38709, WO 98/03473, WO 97/43278, U.S. Pat. Nos. 5,721,251, 5,721,250, WO 98/10653, U.S. Pat. Nos. 5,919,777, 5,830,433 and EP 0995748.

A growth hormone secretagogue is a compound that, when administered to a patient, increases the production and/or secretion of growth hormone when compared with baseline plasma concentrations of growth hormone in a normal healthy individual. Thus, to identify a growth hormone secretagogue, one need simply measure the baseline plasma concentrations of growth hormone over a time period, typically one day, and compare the plasma concentrations of growth hormone after administration of a growth hormone secretagogue with the baseline concentration over the time period. Various examples of growth hormone secretagogues are disclosed herein. It is contemplated that any growth hormone secretagogue can be used in the present administration methods.

The identification of a compound as a "growth hormone secretagogue" which is able to directly or indirectly stimulate or increase the endogenous release of growth hormone in an animal may be readily determined without undue experimentation by methodology well known in the art, such as the assay described by Smith et al., Science, 260, 1640–1643 (1993) (see text of FIG. 2 therein). In a typical experiment, pituitary glands are aseptically removed from 150–200 g Wistar male rats and cultures of pituitary cells are prepared according to Cheng et al., Endocrinol., 124, 2791–2798 (1989). The cells are treated with the subject compound and assayed for growth hormone secreting activity, as described by Cheng et al. (ibid.). In particular, the intrinsic growth hormone secretagogue activity of a compound which may be used in the present invention may be determined by this assay.

The particular application of growth hormone secretagogues in the present invention provides unexpected benefits relative to the administration of exogenous growth hormone. In particular, the growth hormone secretagogue enhances the normal pulsatile release of endogenous growth hormone and thus is more likely to reproduce the natural pattern of endogenous growth hormone release (see J. Clin. Endocrinol. Metab. 81: 4249–4257, 1996). Growth hormone secretagogues which are orally active also have the benefit of being able to be administered orally, rather than just intravenously, intraperitoneally or subcutaneously. The advantage of this method is that, in contrast to injections of growth hormone, it provides a physiological-like pulsatile profile of growth hormone release from the pituitary gland.

The term "patient" means animals, such as humans, companions animals such as dogs, cats and horses, and livestock such as cattle, swine and sheep. Particularly preferred patients are mammals, including both males and females, with humans being even more preferred.

The term "pharmaceutically acceptable" means that a substance or mixture of substances must be compatible with the other ingredients of a formulation, and not deleterious to the patient.

The terms "treating", "treat" or "treatment" include preventive (e.g., prophylactic) and palliative treatment.

The term "therapeutically effective amount" means an amount of a compound that ameliorates, attenuates, or eliminates a particular disease or condition, or prevents or delays the onset of a disease or condition.

In view of their use according to the present invention, the compounds of the present invention may be formulated into various pharmaceutical forms for administration purposes. A compound may be administered, alone or in combination, by oral, parenteral (e.g., intramuscular, intraperitoneal, intravenous or subcutaneous injection, or implant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules and for companion animals the solid dosage forms include an admixture with food and chewable forms. In such solid dosage forms, the compounds and combinations of this invention can be admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings. In the case of chewable forms, the dosage form may comprise flavoring agents and perfuming agents.

Liquid dosage forms for oral administration include pharmaceutically acceptable emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredients in the compositions, methods and combinations of the present invention invention may be varied; however, it is necessary that the amount of the active ingredients be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals. A preferred dosage range in humans is 0.01 to 5.0 mg/kg of body weight daily which can be administered as a single dose or divided into multiple doses.

A preferred dosage range in animals other than humans is 0.01 to 10.0 mg/kg of body weight daily which can be administered as a single dose or divided into multiple doses. A more preferred dosage range in animals other than humans is 0.1 to 5 mg/kg of body weight daily which can be administered as a single dose or divided into multiple doses.

Where the tartrate salt or other pharmaceutically acceptable salt of the above compounds is used in the present invention, the skilled person will be able to calculate effective dosage amounts by calculating the molecular weight of the salt form and performing simple stoichiometric ratios.

Also, the present invention includes within its scope the use of a compound according to the present invention, alone or in combination with a growth hormone secretagogue, such as those referenced herein, including the growth hormone releasing peptides GHRP-6 and GHRP-1 (described in U.S. Pat. No. 4,411,890 and International Patent Applications, Publication Nos. WO 89/07110, WO 89/07111), GHRP-2 (described in WO 93/04081) and B-HT920, as well as hexarelin and growth hormone releasing hormone (GHRH, also designated GRF) and its analogs, growth hormone and its analogs and somatomedins including IGF-I and IGF-II, or in combination with other therapeutic agents, such as α-adrenergic agonists such as clonidine or serotonin 5-HT1D agonists such as sumatriptan, or agents which inhibit somatostatin or its release such as physostigmine and pyridostigmine. Preferably, the compound may be used in combination with growth hormone releasing factor, an analog of growth hormone releasing factor IGF-1 or IGF-II.

Methods to obtain the growth hormone releasing peptides GHRP-6 and GHRP-1 are described in U.S. Pat. No. 4,411,890 and PCT Patent Publications WO 89/07110, WO 89/07111, methods to obtain the growth hormone releasing peptide GHRP-2 are described in PCT Patent Publication WO 93/04081, and methods to obtain hexarelin are described in J. Endocrin. Invest., 15 (Suppl. 4), 45 (1992), all of which are incorporated herein by reference.

In addition, the present invention includes within its scope the use of a pharmaceutical composition according to the present invention comprising, as an active ingredient, at least one compound of the present invention in association with a pharmaceutical vehicle, carrier or diluent.

It will be known to those skilled in the art that other compounds may be used in an effort to stimulate gastrointestinal motility (see R. Faghih et al., Drugs of the Future, 23(8): 861–872 (1998); R. Faghih et al., J. Med. Chem., 41:3402–3408 (1998); H. A. Kirst, Exp. Opin. Ther. Patents, 8(2): 111–120 (1998), which are incorporated herein by reference). Combinations of these therapeutic agents, some of which have been mentioned herein, with a compound of the present invention will bring additional complementary, and often synergistic properties to enhance the desirable properties of these various therapeutic agents. Other prokinetic therapeutic agents, which are therapeutic agents useful for increasing gastrointestinal motility, include, for example, cisapride monohydrate, metoclopramide, erythromycin, domperidone, ondansetron, tropisetron, mosapride and itopride.

In these combinations, the compound of the present invention and the other therapeutic agent(s) may be independently present in the dose ranges from 0.01 to 1 times the dose levels which are effective when these compounds are used singly.

Typically, the individual daily dosages for these combinations may range from about one-fifth of the minimally recommended clinical dosages to the maximum recommended levels for the entities when they are given singly. These dose ranges may be adjusted on a unit basis as necessary to permit divided daily dosage and, as noted above, the dose will vary depending on the nature and severity of the disease, weight of patient, special diets and other factors.

These combinations may be formulated into pharmaceutical compositions as known in the art and as discussed herein. Since the present invention has an aspect that relates to treatment with a combination of active ingredients which may be administered separately, the invention also relates to combining separate pharmaceutical compositions in kit form. The kit comprises two separate pharmaceutical compositions: a compound of the present invention, a prodrug thereof or a pharmaceutically acceptable salt of said compound or said prodrug; and a second therapeutic agent as described herein. The kit comprises a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the dosage form so specified should be ingested. Another example of such a memory aid is a calendar printed on the card e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day. Also, a daily dose of a second therapeutic agent as describe herein can consist of one tablet or capsule while a daily dose of a compound of the present invention, a prodrug thereof or pharmaceutically acceptable salt of said compound or said prodrug can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The utility of the compounds described herein in the methods of the present invention are demonstrated by their activity in one or more of the assays described below:

Assay for Stimulation of Growth Hormone Release from Rat Pituicytes

Compounds having the ability to stimulate GH secretion from cultured rat pituitary cells are identified using the following protocol. This test is also useful for comparison to standards to determine dosage levels.

Cells are isolated from pituitaries of 6-week old male Wistar rats. Following decapitation, the anterior pituitary lobes are removed into cold, sterile Hank's balanced salt solution without calcium or magnesium (HBSS). Tissues are finely minced, then subjected to two cycles of mechanically assisted enzymatic dispersion using 10 U/mL bacterial protease (EC 3.4.24.4, Sigma P-6141, St. Louis, Mo.) in HBSS. The tissue-enzyme mixture is stirred in a spinner flask at 30 rpm in a 5% $CO_2$ atmosphere at 37° C. for 30 min., with manual trituration after 15 min. and 30 min. using a 10-mL pipet. This mixture is centrifuged at 200×g for 5 min. Horse serum (35% final concentration) is added to the supernatant to neutralize excess protease. The pellet is resuspended in fresh protease (10 U/mL), stirred for about 30 min. more under the previous conditions, and manually triturated, ultimately through a 23-gauge needle. Again, horse serum (35% final concentration) is added, then the cells from both digests are combined, pelleted (200×g for about 15 min.), resuspended in culture medium (Dulbecco's Modified Eagle Medium (D-MEM) supplemented with 4.5 g/L glucose, 10% horse serum, 2.5% fetal bovine serum, 1% non-essential amino acids, 100 U/mL nystatin and 50 mg/mL gentamycin sulfate, Gibco, Grand Island, N.Y.) and counted. Cells are plated at 6.0–6.5×10$^4$ cells per cm$^2$ in 48-well Costar™ (Cambridge, Mass.) dishes and cultured for 3–4 days in culture medium.

Just prior to carrying out a GH secretion assay, culture wells are rinsed twice with release medium, then equilibrated for 30 minutes in release medium (D-MEM buffered with 25 mM Hepes, pH 7.4 and containing 0.5% bovine serum albumin at 37° C.). Test compositions are dissolved in DMSO, then diluted into pre-warmed release medium. Assays are typically run in quadruplicate. The assay is initiated by adding 0.5 mL of release medium (with vehicle or test compound) to each culture well. Incubation is carried out at 37° C. for 15 minutes, then terminated by removal of the release medium, which is centrifuged at 2000×g for 15 minutes to remove cellular material. Rat growth hormone concentrations in the supernatants are determined by a-standard radioimmunoassay protocol described below.

Assay for Exogenously-Stimulated Growth Hormone Release in the Rat after Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before testing of a compound of this invention. All rats are allowed access to water and a pelleted commercial diet (Agway Country Food, Syracuse N.Y.) ad libitum.

On the day of the experiment, test compounds are dissolved in vehicle containing 1% ethanol, 1 mM acetic acid and 0.1% bovine serum albumin in saline. Each test is conducted in three rats. Rats are weighed and anesthetized via intraperitoneal injection of sodium pentobarbital (Nembutol®, 50 mg/kg body weight). Fourteen minutes after anesthetic administration, a blood sample is taken by nicking the tip of the tail and allowing the blood to drip into a microcentrifuge tube (baseline blood sample, approximately 100 µl). Fifteen minutes after anesthetic administration, a test compound is delivered by intravenous injection into the tail vein, with a total injection volume of 1 mL/kg body weight. Additional blood samples are taken from the tail at 5, 10 and 15 minutes after administration of a compound of this invention. Blood samples are kept on ice until serum separation by centrifugation (1430×g for 10 minutes at 10° C.). Serum is stored at –80° C. until serum growth hormone determination by radioimmunoassay as described below.

Measurement of Rat Growth Hormone

Rat growth hormone concentrations are determined by double antibody radioimmunoassay using a rat growth hormone reference preparation (NIDDK-rGH-RP-2) and rat growth hormone antiserum raised in monkey (NIDDK-anti-rGH-S-5) obtained from Dr. A. Parlow (Harbor-UCLA Medical Center, Torrance, Calif.). Additional rat growth hormone (1.5 U/mg, #G2414, Scripps Labs, San Diego, Calif.) is iodinated to a specific activity of approximately 30 µCi/µg by the chloramine T method for use as tracer. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation according to methods well known to those skilled in the art. This assay has a working range of 0.08–2.5 µg rat growth hormone per tube.

Assessment of Growth Hormone Release in the Dog after Oral Administration

On the day of dosing, the test compound is weighed out for the appropriate dose and dissolved in water. Doses are delivered at a volume of 0.5–3 mL/kg by oral gavage to 2–4 dogs for each dosing regimen. Blood samples (5 mL) are collected from the jugular vein by direct venipuncture pre-dose and at 0.17, 0.33, 0.5, 0.75, 1, 2, 4, 6, 8 and 24 hours post dose using 5 mL vacutainers containing lithium heparin. The prepared plasma is stored at –20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A. Parlow (Harbor-UCLA Medical Center, Torrence, Calif.). Tracer is produced by chloramine T-iodination of canine growth hormone to a specific activity of 20–40 µCi/µg. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation according to methods well known to those skilled in the art. This assay has a working range of 0.08–2.5 µg canine GH/tube.

Assessment of Canine Growth Hormone and Insulin-Like Growth Factor-1 Levels in the Dog after Chronic Oral Administration The dogs receive test compound daily for either 7 or 14 days. Each day of dosing, the test compound is weighed out for the appropriate dose and dissolved in water. Doses are delivered at a volume of 0.5–3 ml/kg by gavage to 5 dogs for each dosing regimen. Blood samples are collected at days 0, 3, 7, 10 and 14. Blood samples (5 ml) are obtained by direct venipuncture of the jugular vein at pre-dose, 0.17, 0.33, 0.5, 0.75, 1, 2, 3, 6, 8, 12 and 24 hours post administration on days 0, 7 and 14 using 5 ml vacutainers containing lithium heparin for GH determination. In addition, blood is drawn pre-dose and 8 hours after dosing on days 3 and 10 for IGF-I determination. The prepared plasma is stored at −20° C. until analysis.

Plasma samples are extracted with acid ethanol (0.25N HCl in 90% ethanol), centrifuged, then the supernatant is neutralized with tris[hydroxymethyl]amino-methane (registered name is TRIZMA base, manufactured by Sigma Chemical Co.) prior to determination of IGF-I concentration using the Nichols Institute IGF-I extraction kit (San Juan Capistrano, Calif.).

Gastrointestinal Transit in Rats

Male CD Sprague-Dawley rats (175–225 grams) are fitted with tail cups to prevent coprophagy and fasted overnight. The next day the rats are orally given either vehicle (water, 5 ml/kg) or a solution of the test compound in water at doses of 0.1, 0.5, 1 or 5 mg/kg p.o. Fifteen minutes later, the rats are given 1.0 ml of an evaporated milk solution containing 20,000 cpm of $^{51}$Cr as sodium chromate.

The rats are killed 20 minutes after administration of the radioactive marker. The gastroesophageal, pyloric, and ileocecal junctions are ligated, the stomach is removed and the small intestine is divided into ten equal lengths. The stomach and each length of intestine are assayed for radioactivity with a gamma counter. Gastric emptying is determined for each rat by comparing the amount of radioactivity in the intestine relative to the total in the intestine plus stomach. In addition, the geometric center of the distribution of the radioactive marker is used to measure the overall transit rate through the stomach and intestine. Geometric center is calculated as: $\Sigma((\text{fraction of }^{51}\text{Cr per segment}) \times (\text{segment number}))$. For these calculations the stomach is segment number 0 while the ten intestinal segments are designated 1 to 10. Thus, a geometric center of 0.0 would indicate that the entire load of $^{51}$Cr had remained in the stomach.

Results from test compound-treated rats and vehicle-treated rats are compared using one-way ANOVA and Dunnett's test for simultaneous multiple comparisons. The effect of the test compound on gastrointestinal transit in rats is evaluated by measuring gastric emptying and the geometric center of distribution of an orally administered radioactive marker.

At a dose of 0.1 mg/kg, the first test compound, 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, had no effect on gastrointestinal transit. At doses of 0.5, 1.0, and 5.0 mg/kg, the first test compound increased gastric emptying by 25%, 45%, and 49%, respectively (see Table 1 below). A level of gastric emptying greater than 90%, as was seen after the 1 mg/kg and 5 mg/kg doses (92% and 94%, respectively), is considered maximal. The increases in geometric centers (a measure of transit through both the stomach and small intestine) were 39% at 0.5 mg/kg, 67% at 1 mg/kg and 68% at 5 mg/kg.

TABLE 1

Effect of Oral First Test Compound on Gastrointestinal Transit in the Rat.
A $^{51}$Cr-containing solution was administered to rats 15 minutes after oral administration of the first test compound or water. Twenty minutes later, the stomach and small intestine, divided into ten segments of equal length, were assayed for radioactivity. Gastric emptying = % of total $^{51}$Cr in the intestine; geometric center = $\Sigma((\text{fraction of }^{51}\text{Cr per segment}) \times (\text{segment number}))$. Data shown are mean ± SEM.

| Treatment | | N | % Gastric Emptying | Geometric Center |
|---|---|---|---|---|
| Vehicle | (water) | 15 | 63.0 ± 2.4 | 2.89 ± 0.13 |
| 1$^{st}$ test compound | | | | |
| | 0.1 mg/kg | 8 | 62.5 ± 3.4 | 2.82 ± 0.17 |
| | 0.5 mg/kg | 8 | *79.0 ± 4.2 | *4.03 ± 0.26 |
| | 1 mg/kg | 7 | *91.5 ± 1.6 | *4.81 ± 0.21 |
| | 5 mg/kg | 7 | *93.7 ± 1.4 | *4.85 ± 0.19 |

*$p < 0.05$ compared to vehicle group by Dunnett's multiple comparison test.

An oral dose of 0.1 mg/kg of the second test compound, 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide, had no effect on gastrointestinal transit. Doses of 0.5,1, and 5 mg/kg increased both gastric emptying and the transport through the upper GI tract. At doses of 0.5, 1.0, and 5.0 mg/kg, the second test compound increased gastric emptying by 21%, 37%, and 34%, respectively (see Table 2 below). The increases in geometric centers (a measure of transit through both the stomach and small intestine) were 37% at 0.5 mg/kg, 50% at 1 mg/kg and 42% at 5 mg/kg.

TABLE 2

Effect of Oral Second Test Compound on Gastrointestinal Transit in the Rat.
A $^{51}$Cr-containing solution was administered to rats 15 minutes after oral administration of the second test compound or water. Twenty minutes later, the stomach and small intestine, divided into ten segments of equal length, were assayed for radioactivity. Gastric emptying = % of total $^{51}$Cr in the intestine; geometric center = $\Sigma((\text{fraction of }^{51}\text{Cr per segment}) \times (\text{segment number}))$. Data shown are mean ± SEM.

| Treatment | | N | % Gastric Emptying | Geometric Center |
|---|---|---|---|---|
| Vehicle | (water) | 11 | 65.8 ± 4.1 | 2.9 ± 0.2 |
| 2$^{nd}$ Test Compound | | | | |
| | 0.1 mg/kg | 9 | 68.9 ± 3.4 | 3.1 ± 0.2 |
| | 0.5 mg/kg | 10 | *79.5 ± 3.6 | *3.9 ± 0.3 |
| | 1 mg/kg | 9 | *89.9 ± 2.3 | *4.3 ± 0.2 |
| | 5 mg/kg | 11 | *88.3 ± 2.4 | *4.1 ± 0.2 |

*$p < 0.05$ compared to vehicle group by Dunnett's multiple comparison test.

While the foregoing description discloses the present invention, with examples provided for the purpose of illustration, it will be understood that the practice of the present invention encompasses all of the usual variations, adaptations or modifications as come within the scope of the following claims and their equivalents.

What is claimed is:

1. A kit for treating a condition selected from the group consisting of gastroesophageal reflux disease, gastroparesis, postoperative ileus, emesis, constipation and colonic pseudo-obstruction, the kit comprising:

a) a first pharmaceutical composition comprising a compound of Formula I

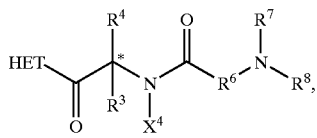

or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, or a tautomer thereof,
wherein:
HET is a heterocyclic moiety selected from the group consisting of

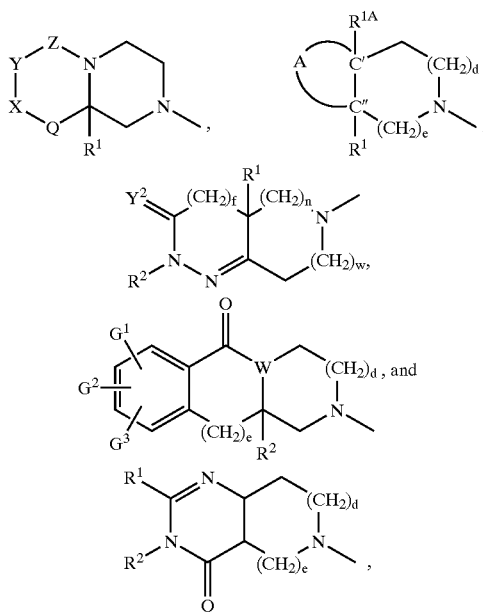

d is 0, 1 or 2;
e is 1 or 2;
f is 0 or 1;
n and w are 0, 1 or 2, provided that n and w cannot both be 0 at the same time;
$Y^2$ is oxygen or sulfur;
A is a divalent radical, where the left hand side of the radical as shown below is connected to C'' and the right hand side of the radical as shown below is connected to C', selected from the group consisting of
—$NR^2$—C(O)—$NR^2$—, —$NR^2$—$S(O)_2$—$NR^2$—, —O—C(O)—$NR^2$—, —$NR^2$—C(O)—O—, —C(O)—$NR^2$—C(O)—, —C(O)—$NR^2$—C($R^9R^{10}$)—, —C($R^9R^{10}$)—$NR^2$—C(O)—, —C($R^9R^{10}$)—C($R^9R^{10}$)—C($R^9R^{10}$)—, —$S(O)_2$—C($R^9R^{10}$)—C($R^9R^{10}$)—, —C($R^9R^{10}$)—O—C(O)—, —C($R^9R^{10}$)—O—C($R^9R^{10}$)—, —$NR^2$—C(O)—C($R^9R^{10}$)—, —O—C(O)—C($R^9R^{10}$)—, —C($R^9R^{10}$)—C(O)—$NR^2$—, —C($R^9R^{10}$)—C(O)—O—, —C(O)—$NR^2$—C($R^9R^{10}$)—C($R^9R^{10}$)—, —C(O)—O—C($R^9R^{10}$)—, —C($R^9R^{10}$)—C($R^9R^{10}$)—C($R^9R^{10}$)—$NR^2$—, —$S(O)_2$—$NR^2$—C($R^9R^{10}$)—C($R^9R^{10}$)—, —C($R^9R^{10}$)—C($R^9R^{10}$)—C($R^9R^{10}$)—C($R^9R^{10}$)—$NR^2$—C(O)—, —C($R^9R^{10}$)—$NR^2$—C(O)—, —C($R^9R^{10}$)—$NR^2$—C(O)—, —$NR^2$—C(O)—C($R^9R^{10}$)—C($R^9R^{10}$)—, —$NR^2$—$S(O)_2$—C($R^9R^{10}$)—C($R^9R^{10}$)—, —O—C(O)—C($R^9R^{10}$)—C($R^9R^{10}$)—, —C($R^9R^{10}$)—C($R^9R^{10}$)—C(O)—, —C($R^9R^{10}$)—C($R^9R^{10}$)—C(O)—$NR^2$—, —C($R^9R^{10}$)—C($R^9R^{10}$)—C(O)—, —C($R^9R^{10}$)—C(O)—$NR^2$—C(O)—, —$NR^2$—C(O)—$NR^2$—C($R^9R^{10}$)—, —$NR^2$—$S(O)_2$—$NR^2$—C($R^9R^{10}$)—, —O—C(O)—$NR^2$—C($R^9R^{10}$)—, —C(O)—N=C($R^{11}$)—$NR^2$—, —C(O)—$NR^2$—C($R^{11}$)=N—, —C($R^9R^{10}$)—$NR^{12}$—C($R^9R^{10}$)—, —$NR^{12}$—C($R^9R^{10}$)—, —$NR^{12}$—C($R^9R^{10}$)—C($R^9R^{10}$)—, —C(O)—O—C($R^9R^{10}$)—C($R^9R^{10}$)—, —$NR^2$—C($R^{11}$)=N—C(O)—, —C($R^9R^{10}$)—C($R^9R^{10}$)—N($R^{12}$)—, —C($R^9R^{10}$)—$NR^{12}$—, —N=C($R^{11}$)—$NR^2$—C(O)—, —C($R^9R^{10}$)—C($R^9R^{10}$)—$NR^2$—$S(O)_2$—, —C($R^9R^{10}$)—C($R^9R^{10}$)—$S(O)_2$—$NR^2$—, —C($R^9R^{10}$)—C($R^9R^{10}$)—C(O)—O—, —C($R^9R^{10}$)—$S(O)_2$—C($R^9R^{10}$)—, —C($R^9R^{10}$)—C($R^9R^{10}$)—$S(O)_2$—, —O—C($R^9R^{10}$)—C($R^9R^{10}$)—, —C($R^9R^{10}$)—C($R^9R^{10}$)—O—, —C($R^9R^{10}$)—CO—C($R^9R^{10}$)—, —C(O)—C($R^9R^{10}$)—C($R^9R^{10}$)— and —C($R^9R^{10}$)—$NR^2$—$S(O)_2$—$NR^2$—;
Q is a covalent bond or $CH_2$;
W is CH or N;
X is $CR^9R^{10}$, C=$CH_2$ or C=O;
Y is $CR^9R^{10}$, O or $NR^2$;
Z is C=O, C=S or $S(O)_2$;
$G^1$ is hydrogen, halo, hydroxy, nitro, amino, cyano, phenyl, carboxyl, —$CONH_2$, —($C_1$-$C_4$)alkyl optionally independently substituted with one or more phenyl, one or more halogens or one or more hydroxy groups, —($C_1$-$C_4$)alkoxy optionally independently substituted with one or more phenyl, one or more halogens or one or more hydroxy groups, —($C_1$-$C_4$)alkylthio, phenoxy, —COO($C_1$-$C_4$)alkyl, N,N-di-($C_1$-$C_4$)alkylamino, —($C_2$-$C_6$)alkenyl optionally independently substituted with one or more phenyl, one or more halogens or one or more hydroxy groups, —($C_2$-$C_6$) alkynyl optionally independently substituted with one or more phenyl, one or more halogens or one or more hydroxy groups, —($C_3$-$C_6$)cycloalkyl optionally independently substituted with one or more ($C_1$-$C_4$)alkyl groups, one or more halogens or one or more hydroxy groups, —($C_1$-$C_4$) alkylamino carbonyl or di-($C_1$-$C_4$)alkylamino carbonyl;
$G^2$ and $G^3$ are each independently selected from the group consisting of hydrogen, halo, hydroxy, —($C_1$-$C_4$)alkyl optionally independently substituted with one to three halo groups and —($C_1$-$C_4$)alkoxy optionally independently substituted with one to three halo groups;
$R^1$ is hydrogen, —CN, —$(CH_2)_q$N($X^6$)C(O)$X^6$, —$(CH_2)_q$N($X^6$)C(O)$(CH_2)_t$—$A^1$, —$(CH_2)_q$N($X^6$)$S(O)_2(CH_2)_t$—$A^1$, —$(CH_2)_q$N($X^6$)$S(O)_2X^6$, —$(CH_2)_q$N($X^6$)C(O)N($X^6$)$(CH_2)_t$—$A^1$, —$(CH_2)_q$N($X^6$)C(O)N($X^6$)($X^6$), —$(CH_2)_q$C(O)N($X^6$)($X^6$), —$(CH_2)_q$C(O)N($X^6$)$(CH_2)_t$—$A^1$, —$(CH_2)_q$C(O)$OX^6$, —$(CH_2)_q$C(O)O$(CH_2)_t$—$A^1$, —$(CH_2)_q$$OX^6$, —$(CH_2)_q$OC(O)$X^6$, —$(CH_2)_q$OC(O)$(CH_2)_t$—$A^1$, —$(CH_2)_q$OC(O)N($X^6$)$(CH_2)_t$—$A^1$, —$(CH_2)_q$OC(O)N($X^6$)($X^6$), —$(CH_2)_q$C(O)$X^6$, —$(CH_2)_q$C(O)$(CH_2)_t$—$A^1$, —$(CH_2)_q$N($X^6$)C(O)$OX^6$, —$(CH_2)_q$N($X^6$)$S(O)_2$N($X^6$)($X^6$), —$(CH_2)_q$S(O)$_m$$X^6$, —$(CH_2)_q$S(O)$_m$$(CH_2)_t$—$A^1$, —($C_1$-$C_{10}$)alkyl, —$(CH_2)_t$—$A^1$, —$(CH_2)_q$—($C_3$-$C_7$)cycloalkyl, —$(CH_2)_q$—$Y^1$—($C_1$-$C_6$)alkyl, —$(CH_2)_q$—$Y^1$—$(CH_2)_t$—$A^1$ or —$(CH_2)_q$—$Y^1$—$(CH_2)_t$—($C_3$-$C_7$)cycloalkyl;
where the alkyl and cycloalkyl groups in the definition of $R^1$ are optionally substituted with ($C_1$-$C_4$)alkyl, hydroxy, ($C_1$-$C_4$)alkoxy, carboxyl, —$CONH_2$, —S(O)$_m$ ($C_1$-$C_6$)alkyl, —$CO_2$($C_1$-$C_4$)alkyl ester, 1H-tetrazol-5-yl or 1, 2 or 3 fluoro groups;
$Y^1$ is O, S(O)$_m$, —C(O)N$X^6$, —CH=CH—, —C≡C—, —N($X^6$)C(O)—, —C(O)N$X^6$—, —C(O)O—, —OC(O)N($X^6$)— or —OC(O)—;

q is 0, 1, 2, 3 or 4;

t is 0, 1, 2 or 3;

said $(CH_2)_q$ group and $(CH_2)_t$ group in the definition of $R^1$ are optionally independently substituted with hydroxy, $(C_1-C_4)$alkoxy, carboxyl, —$CONH_2$, —$S(O)_m(C_1-C_6)$alkyl, —$CO_2(C_1-C_4)$alkyl ester, 1H-tetrazol-5-yl, 1, 2 or 3 fluoro groups or 1 or 2 $(C_1-C_4)$alkyl groups;

$R^{1A}$ is selected from the group consisting of hydrogen, F, Cl, Br, I, $(C_1-C_6)$alkyl, phenyl$(C_1-C_3)$alkyl, pyridyl$(C_1-C_3)$alkyl, thiazolyl$(C_1-C_3)$alkyl and thienyl$(C_1-C_3)$alkyl, provided that $R^{1A}$ is not F, Cl, Br or I when a heteroatom is vicinal to C";

$R^2$ is hydrogen, $(C_1-C_8)$alkyl, —$(C_0-C_3)$alkyl-$(C_3-C_8)$cycloalkyl, —$(C_1-C_4)$alkyl-$A^1$ or $A^1$;

where the alkyl groups and the cycloalkyl groups in the definition of $R^2$ are optionally substituted with hydroxy, —$C(O)OX^6$, —$C(O)N(X^6)(X^6)$, —$N(X^6)(X^6)$, —$S(O)_m(C_1-C_6)$alkyl, —$C(O)A^1$, —$C(O)(X^6)$, $CF_3$, CN or 1, 2 or 3 independently selected halo groups;

$R^3$ is selected from the group consisting of $A^1$, $(C_1-C_{10})$alkyl, —$(C_1-C_6)$alkyl-$A^1$, —$(C_1-C_6)$alkyl-$(C_3-C_7)$cycloalkyl, —$(C_1-C_5)$alkyl-$X^1$—$(C_1-C_5)$alkyl, —$(C_1-C_5)$alkyl-$X^1$—$(C_0-C_5)$alkyl-$A^1$ and —$(C_1-C_5)$alkyl-$X^1$—$(C_1-C_5)$alkyl-$(C_3-C_7)$cycloalkyl;

where the alkyl groups in the definition of $R^3$ are optionally substituted with —$S(O)_m(C_1-C_6)$alkyl, —$C(O)OX^3$, 1, 2, 3, 4 or 5 independently selected halo groups or 1, 2 or 3 independently selected —$OX^3$ groups;

$X^1$ is O, $S(O)_m$, —$N(X^2)C(O)$—, —$C(O)N(X^2)$—, —$OC(O)$—, —$C(O)O$—, —$CX^2=CX^2$—, —$N(X^2)C(O)O$—, —$OC(O)N(X^2)$— or —C≡C—;

$R^4$ is hydrogen, $(C_1-C_6)$alkyl or $(C_3-C_7)$cycloalkyl, or $R^4$ is taken together with $R^3$ and the carbon atom to which they are attached and form $(C_5-C_7)$cycloalkyl, $(C_5-C_7)$cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;

$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;

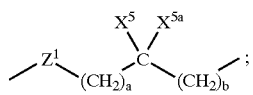

$R^6$ is a bond or is where a and b are each independently 0, 1, 2 or 3;

$X^5$ and $X^{5a}$ are each independently selected from the group consisting of hydrogen, $CF_3$, $A^1$ and optionally substituted $(C_1-C_6)$alkyl;

the optionally substituted $(C_1-C_6)$alkyl in the definition of $X^5$ and $X^{5a}$ is optionally substituted with a substituent selected from the group consisting of $A^1$, $OX^2$, —$S(O)_m(C_1-C_6)$alkyl, —$C(O)OX^2$, $(C_3-C_7)$cycloalkyl, —$N(X^2)(X^2)$ and —$C(O)N(X^2)(X^2)$;

or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then only one of $X^5$ or $X^{5a}$ is on the carbon atom and only one of $R^7$ or $R^8$ is on the nitrogen atom and further provided that when two alkylene bridges are formed then $X^5$ and $X^{5a}$ cannot be on the carbon atom and $R^7$ and $R^8$ cannot be on the nitrogen atom;

or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a bond, O or N—$X^2$, provided that when a and b are both 0 then $Z^1$ is not N—$X^2$ or O;

or $R^6$ is —$(CR^aR^b)_a$—E—$(CR^aR^b)_b$—, where the —$(CR^aR^b)_a$— group is attached to the carbonyl carbon of the amide group of the compound of formula I and the —$(CR^aR^b)_b$ group is attached to the terminal nitrogen atom of the compound of formula I;

E is —O—, —S—, —CH=CH— or an aromatic moiety selected from

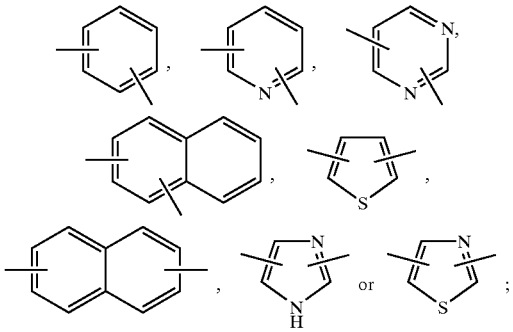

said aromatic moiety in the definition of E optionally substituted with up to three halo, hydroxy, —$N(R^c)(R^c)$, $(C_1-C_6)$alkyl or $(C_1-C_6)$alkoxy;

$R^a$ and $R^b$ are, for each occurrence, independently hydrogen, $(C_1-C_6)$alkyl, trifluoromethyl, phenyl or monosubstituted $(C_1-C_6)$alkyl where the substituents are imidazolyl, naphthyl, phenyl, indolyl, p-hydroxyphenyl, —$OR^c$, $S(O)_mR^c$, $C(O)OR^c$, $(C_3-C_7)$cycloalkyl, —$N(R^c)(R^c)$, —$C(O)N(R^c)(R^c)$, or $R^a$ or $R^b$ may independently be joined to one or both of $R^7$ or E (where E is other than O, S or —CH=CH—) to form an alkylene bridge between the terminal nitrogen and the alkyl portion of the $R^a$ or $R^b$ and the $R^7$ or E group, wherein the bridge contains 1 to 8 carbon atoms; or $R^a$ and $R^b$ may be joined to one another to form a $(C_3-C_7)$cycloalkyl;

$R^c$, for each occurrence, is independently hydrogen or $(C_1-C_6)$alkyl;

a and b are independently 0, 1, 2 or 3, with the proviso that if E is —O— or —S—, b is other than 0 or 1 and with the further proviso that if E is —CH=CH—, b is other than 0;

$R^7$ and $R^8$ are each independently hydrogen or optionally substituted $(C_1-C_6)$alkyl;
  where the optionally substituted $(C_1-C_6)$alkyl in the definition of $R^7$ and $R^8$ is optionally independently substituted with $A^1$, —C(O)O—$(C_1-C_6)$alkyl, —S(O)$_m$ $(C_1-C_6)$alkyl, 1 to 5 halo groups, 1 to 3 hydroxy groups, 1 to 3 —O—C(O)$(C_1-C_{10})$alkyl groups or 1 to 3 $(C_1-C_6)$alkoxy groups; or
$R^7$ and $R^8$ can be taken together to form —(CH$_2$)$_r$—L—(CH$_2$)$_r$—;
  where L is C(X$^2$)(X$^2$), S(O)$_m$ or N(X$^2$);
$R^9$ and $R^{10}$ are each independently selected from the group consisting of hydrogen, fluoro, hydroxy and $(C_1-C_5)$alkyl optionally independently substituted with 1–5 halo groups;
$R^{11}$ is selected from the group consisting of $(C_1-C_5)$alkyl and phenyl optionally substituted with 1–3 substitutents each independently selected from the group consisting of $(C_1-C_5)$alkyl, halo and $(C_1-C_5)$alkoxy;
$R^{12}$ is selected from the group consisting of $(C_1-C_5)$ alkylsulfonyl, $(C_1-C_5)$alkanoyl and $(C_1-C_5)$alkyl where the alkyl portion is optionally independently substituted by 1–5 halo groups;
$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;
  $A^1$ for each occurrence is independently optionally substituted, on one or optionally both rings if $A^1$ is a bicyclic ring system, with up to three substituents, each substituent independently selected from the group consisting of F, Cl, Br, I, OCF$_3$, OCF$_2$H, CF$_3$, CH$_3$, OCH$_3$, —OX$^6$, —C(O)N(X$^6$)(X$^6$), —C(O)OX$^6$, oxo, $(C_1-C_6)$ alkyl, nitro, cyano, benzyl, —S(O)$_m(C_1-C_6)$alkyl, 1H-tetrazol-5-yl, phenyl, phenoxy, phenylalkyloxy, halophenyl, methylenedioxy, —N(X$^6$)(X$^6$), —N(X$^6$)C(O)(X$^6$), —S(O)$_2$N(X$^6$)(X$^6$), —N(X$^6$)S(O)$_2$-phenyl, —N(X$^6$)S(O)$_2$X$^6$, —CONX$^{11}$X$^{12}$, —S(O)$_2$NX$^{11}$X$^{12}$, —NX$^6$S(O)$_2$X$^{12}$, —NX$^6$CONX$^{11}$X$^{12}$, —NX$^6$S(O)$_2$ NX$^{11}$X$^{12}$, —NX$^6$C(O)X$^{12}$, imidazolyl, thiazolyl and tetrazolyl, provided that if $A^1$ is optionally substituted with methylenedioxy then it can only be substituted with one methylenedioxy;
    where X$^{11}$ is hydrogen or optionally substituted $(C_1-C_6)$alkyl;
    the optionally substituted $(C_1-C_6)$alkyl defined for X$^{11}$ is optionally independently substituted with phenyl, phenoxy, $(C_1-C_6)$alkoxycarbonyl, —S(O)$_m(C_1-C_6)$alkyl, 1 to 5 halo groups, 1 to 3 hydroxy groups, 1 to 3 $(C_1-C_{10})$alkanoyloxy groups or 1 to 3 $(C_1-C_6)$alkoxy groups;
    X$^{12}$ is hydrogen, $(C_1-C_6)$alkyl, phenyl, thiazolyl, imidazolyl, furyl or thienyl, provided that when X$^{12}$ is not hydrogen, the X$^{12}$ group is optionally substituted with one to three substituents independently selected from the group consisting of Cl, F, CH$_3$, OCH$_3$, OCF$_3$ and CF$_3$;
    or X$^{11}$ and X$^{12}$ are taken together to form —(CH$_2$)$_r$—L$^1$—(CH$_2$)$_r$—;

L$^1$ is C(X$^2$)(X$^2$), O, S(O)$_m$ or N(X$^2$);
r for each occurrence is independently 1, 2 or 3;
X$^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of X$^2$ are optionally independently substituted with —S(O)$_m(C_1-C_6)$alkyl, —C(O)OX$^3$, 1 to 5 halo groups or 1–3 OX$^3$ groups;
X$^3$ for each occurrence is independently hydrogen or $(C_1-C_6)$alkyl;
X$^6$ for each occurrence is independently hydrogen, optionally substituted $(C_1-C_6)$alkyl, $(C_2-C_6)$halogenated alkyl, optionally substituted $(C_3-C_7)$cycloalkyl, $(C_3-C_7)$-halogenated cycloalkyl, where optionally substituted $(C_1-C_6)$alkyl and optionally substituted $(C_3-C_7)$cycloalkyl in the definition of X$^6$ is optionally independently mono- or di-substituted with $(C_1-C_4)$alkyl, hydroxy, $(C_1-C_4)$alkoxy, carboxyl, CONH$_2$, —S(O)$_m(C_1-C_6)$alkyl, carboxylate $(C_1-C_4)$alkyl ester or 1H-tetrazol-5-yl; or when there are two X$^6$ groups on one atom and both X$^6$ are independently $(C_1-C_6)$alkyl, the two $(C_1-C_6)$alkyl groups may be optionally joined and, together with the atom to which the two X$^6$ groups are attached, form a 4- to 9-membered ring optionally having oxygen, sulfur or NX$^7$ as a ring member;
  X$^7$ is hydrogen or $(C_1-C_6)$alkyl optionally substituted with hydroxy;
m for each occurrence is independently 0, 1 or 2;
with the provisos that:
1) X$^6$ and X$^{12}$ cannot be hydrogen when attached to C(O) or S(O)$_2$ in the form C(O)X$^6$, C(O)X$^{12}$, S(O)$_2$X$^6$ or S(O)$_2$X$^{12}$; and
2) when $R^6$ is a bond then L is N(X$^2$) and each r in the definition —(CH$_2$)$_r$—L—(CH$_2$)$_r$— is independently 2 or 3.
  b) a second pharmaceutical composition comprising a prokinetic agent; and
  c) a container.
2. A kit according to claim 1 wherein the first pharmaceutical composition comprises a compound of the Formula I-A

I-A a racemic-diastereomeric mixture or an optical isomer of said compound or a pharmaceutically-acceptable salt or prodrug thereof, or a tautomer thereof, wherein
f is 0;
n is 0 and w is 2, or n is 1 and w is 1, or n is 2 and w is 0;
Y is oxygen or sulfur;
$R^1$ is hydrogen, —CN, —(CH$_2$)$_q$N(X$^6$)C(O)X$^6$, —(CH$_2$)$_q$N (X$^6$)C(O)(CH$_2$)$_t$—A$^1$, —(CH$_2$)$_q$N(X$^6$)SO$_2$(CH$_2$)$_t$—A$^1$, —(CH$_2$)$_q$N(X$^6$)SO$_2$X$^6$, —(CH$_2$)$_q$N(X$^6$)C(O)N(X$^6$)(CH$_2$)$_t$ —A$^1$, —(CH$_2$)$_q$N(X$^6$)C(O)N(X$^6$)(X$^6$), —(CH$_2$)$_q$C(O)N (X$^6$)(X$^6$), —(CH$_2$)$_q$C(O)N(X$^6$)(CH$_2$)$_t$—A$^1$, —(CH$_2$)$_q$C(O) OX$^6$, —(CH$_2$)$_q$C(O)O(CH$_2$)$_t$—A$^1$, —(CH$_2$)$_q$OX$^6$, —(CH$_2$)$_q$ OC(O)X$^6$, —(CH$_2$)$_q$OC(O)(CH$_2$)$_t$—A$^1$, —(CH$_2$)$_q$ OC(O)N(X$^6$)(CH$_2$)$_t$—A$^1$, —(CH$_2$)$_q$OC(O)N(X$^6$) (X$^6$), —(CH$_2$)$_q$C(O)X$^6$, —(CH$_2$)$_q$C(O)(CH$_2$)$_t$—A$^1$, —(CH$_2$)$_q$N(X$^6$)C(O)OX$^6$, —(CH$_2$)$_q$N(X$^6$)SO$_2$N(X$^6$)(X$^6$), —(CH$_2$)$_q$S(O)$_m$X$^6$, —(CH$_2$)$_q$S(O)$_m$(CH$_2$)$_t$—A$^1$, —($C_1$–$C_{10}$)alkyl, —$(CH_2)_t$—$A^1$, —$(CH_2)_q$—($C_3$–$C_7$)cycloalkyl, —$(CH_2)_q$—$Y^1$—($C_1$–$C_6$)alkyl, —$(CH_2)_q$—$Y^1$—$(CH_2)_t$—$A^1$ or —$(CH_2)_q$—$Y^1$—$(CH_2)_t$—($C_3$–$C_7$)cycloalkyl;

where the alkyl and cycloalkyl groups in the definition of $R^1$ are optionally substituted with ($C_1$–$C_4$)alkyl, hydroxyl, ($C_1$–$C_4$)alkoxy, carboxyl, —$CONH_2$, —$S(O)_m$($C_1$–$C_6$)alkyl, —$CO_2$($C_1$–$C_4$)alkyl ester, 1H-tetrazol-5-yl or 1, 2 or 3 fluoro;

$Y^1$ is O, $S(O)_m$, —$C(O)NX^6$—, —CH=CH—, —C≡C—, —$N(X^6)C(O)$—, —C(O)O—, —OC(O)N($X^6$)— or —OC(O)—;

q is 0, 1, 2, 3 or 4;

t is 0, 1, 2 or 3;

said $(CH_2)_q$ group and $(CH_2)_t$ group may each be optionally substituted with hydroxyl, ($C_1$–$C_4$)alkoxy, carboxyl, —$CONH_2$, —$S(O)_m$($C_1$–$C_6$)alkyl, —$CO_2$($C_1$–$C_4$)alkyl ester, 1H-tetrazol-5-yl, 1, 2 or 3 fluoro, or 1 or 2 ($C_1$–$C_4$)alkyl;

$R^2$ is hydrogen, ($C_1$–$C_8$)alkyl, —($C_0$–$C_3$)alkyl-($C_3$–$C_8$)cycloalkyl, —($C_1$–$C_4$)alkyl-$A^1$ or $A^1$;

where the alkyl groups and the cycloalkyl groups in the definition of $R^2$ are optionally substituted with hydroxyl, —$C(O)OX^6$, —$C(O)N(X^6)(X^6)$, —$N(X^6)(X^6)$, —$S(O)_m$($C_1$–$C_6$)alkyl, —$C(O)A^1$, —$C(O)(X^6)$, $CF_3$, CN or 1, 2 or 3 halogen;

$R^3$ is $A^1$, ($C_1$–$C_{10}$)alkyl, —($C_1$–$C_6$)alkyl-$A^1$, —($C_1$–$C_6$)alkyl-($C_3$–$C_7$)cycloalkyl, —($C_1$–$C_5$)alkyl-$X^1$—($C_1$–$C_5$)alkyl, —($C_1$–$C_5$)alkyl-$X^1$—($C_0$–$C_5$)alkyl-$A^1$ or —($C_1$–$C_5$)alkyl-$X^1$—($C_1$–$C_5$)alkyl-($C_3$–$C_7$)cycloalkyl;

where the alkyl groups in the definition of $R^3$ are optionally substituted with, —$S(O)_m$($C_1$–$C_6$)alkyl, —$C(O)OX^3$, 1, 2, 3, 4 or 5 halogens, or 1, 2 or 3 $OX^3$;

$X^1$ is O, $S(O)_m$, —$N(X^2)C(O)$—, —$C(O)N(X^2)$—, —OC(O)—, —C(O)O—, —$CX^2$=$CX^2$—, —$N(X^2)C(O)O$—, —$OC(O)N(X^2)$— or —C≡C—;

$R^4$ is hydrogen, ($C_1$–$C_6$)alkyl or ($C_3$–$C_7$)cycloalkyl;

$X^4$ is hydrogen or ($C_1$–$C_6$)alkyl or $X^4$ is taken together with $R^4$ and the nitrogen atom to which $X^4$ is attached and the carbon atom to which $R^4$ is attached and form a five to seven membered ring;

$R^6$ is a bond or is

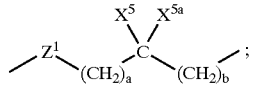

where a and b are independently 0, 1, 2 or 3;

$X^5$ and $X^{5a}$ are each independently selected from the group consisting of hydrogen, trifluoromethyl, $A^1$ and optionally substituted ($C_1$–$C_6$)alkyl;

the optionally substituted ($C_1$–$C_6$)alkyl in the definition of $X^5$ and $X^{5a}$ is optionally substituted with a substituent selected from the group consisting of $A^1$, $OX^2$, —$S(O)_m$($C_1$–$C_6$)alkyl, —$C(O)OX^2$, ($C_3$–$C_7$)cycloalkyl, —$N(X^2)(X^2)$ and —$C(O)N(X^2)(X^2)$;

$R^7$ and $R^8$ are independently hydrogen or optionally substituted ($C_1$–$C_6$)alkyl;

where the optionally substituted ($C_1$–$C_6$)alkyl in the definition of $R^7$ and $R^8$ is optionally independently substituted with $A^1$, —C(O)O—($C_1$–$C_6$)alkyl, —$S(O)_m$($C_1$–$C_6$)alkyl, 1 to 5 halogens, 1 to 3 hydroxy, 1 to 3 —O—C(O)($C_1$–$C_{10}$)alkyl or 1 to 3 ($C_1$–$C_6$)alkoxy; or $R^7$ and $R^8$ can be taken together to form —$(CH_2)_r$—L—$(CH_2)_r$—;

where L is $C(X^2)(X^2)$, $S(O)_m$ or $N(X^2)$;

$A^1$ in the definition of $R^1$ is a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ in the definition of $R^2$, $R^3$, $R^6$, $R^7$ and $R^8$ is independently ($C_5$–$C_7$)cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, in one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —$C(O)N(X^6)(X^6)$, —$C(O)OX^6$, oxo, ($C_1$–$C_6$)alkyl, nitro, cyano, benzyl, —$S(O)_m$($C_1$–$C_6$)alkyl, 1H-tetrazol-5-yl, phenyl, phenoxy, phenylalkyloxy, halophenyl, methylenedioxy, —N ($X^6$)($X^6$), —$N(X^6)C(O)(X^6)$, —$SO_2N(X^6)(X^6)$, —$N(X^6)SO_2$-phenyl, —$N(X^6)SO_2X^6$, —$CONX^{11}X^{12}$, —$SO_2NX^{11}X^{12}$, —$NX^6SO_2X^{12}$, —$NX^6CONX^{11}X^{12}$, —$NX^6SO_2NX^{11}X^{12}$, —$NX^6C(O)X^{12}$, imidazolyl, thiazolyl or tetrazolyl, provided that if $A^1$ is optionally substituted with methylenedioxy then it can only be substituted with one methylenedioxy;

where $X^{11}$ is hydrogen or optionally substituted ($C_1$–$C_6$)alkyl;

the optionally substituted ($C_1$–$C_6$)alkyl defined for $X^{11}$ is optionally independently substituted with phenyl, phenoxy, ($C_1$–$C_6$)alkoxycarbonyl, —$S(O)_m$ ($C_1$–$C_6$)alkyl 1 to 5 halogens, 1 to 3 hydroxy, 1 to 3 ($C_1$–$C_{10}$)alkanoyloxy or 1 to 3 ($C_1$–$C_6$)alkoxy;

$X^{12}$ is hydrogen, ($C_1$–$C_6$)alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$;

or $X^{11}$ and $X^{12}$ are taken together to form —$(CH_2)_r$—$L^1$—$(CH_2)_r$—;

where $L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted ($C_1$–$C_6$)alkyl, or optionally substituted ($C_3$–$C_7$)cycloalkyl, where the optionally substituted ($C_1$–$C_6$)alkyl and optionally substituted ($C_3$–$C_7$)cycloalkyl in the definition of $X^2$ are optionally independently substituted with —$S(O)_m$($C_1$–$C_6$)alkyl, —$C(O)OX^3$, 1 to 5 halogens or 1–3 $OX^3$;

$X^3$ for each occurrence is independently hydrogen or $(C_1-C_6)$alkyl;

$X^6$ is independently hydrogen, optionally substituted $(C_1-C_6)$alkyl, $(C_2-C_6)$halogenated alkyl, optionally substituted $(C_3-C_7)$cycloalkyl, $(C_3-C_7)$-halogenatedcycloalkyl, where optionally substituted $(C_1-C_6)$alkyl and optionally substituted $(C_3-C_7)$cycloalkyl in the definition of $X^6$ is optionally independently substituted by 1 or 2 $(C_1-C_4)$alkyl, hydroxyl, $(C_1-C_4)$alkoxy, carboxyl, $CONH_2$, $-S(O)_m(C_1-C_6)$alkyl, carboxylate $(C_1-C_4)$alkyl ester, or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$;

$X^7$ is hydrogen or $(C_1-C_6)$alkyl optionally substituted with hydroxyl; and m for each occurrence is independently 0, 1 or 2;

with the proviso that:

$X^6$ and $X^{12}$ cannot be hydrogen when it is attached to C(O) or $SO_2$ in the form $C(O)X^6$, $C(O)X^{12}$, $SO_2X^6$ or $SO_2X^{12}$; and when $R^6$ is a bond then L is $N(X^2)$ and each r in the definition $-(CH_2)_r-L-(CH_2)_r-$ is independently 2 or 3.

3. A kit according to claim 2 wherein the first pharmaceutical composition comprises the compound 2-amino-N-(2-(3a -(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug thereof or a pharmaceutically acceptable salt of said compound or said prodrug.

4. A kit according to claim 3 wherein the first pharmaceutical composition comprises the compound 2-amino-N-[2-(3a -(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide, L-tartrate.

5. A kit according to claim 2 wherein the first pharmaceutical composition comprises the compound 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide, a prodrug thereof or a pharmaceutically acceptable salt of said compound or said prodrug.

6. A kit according to claim 5 wherein the first pharmaceutical composition comprises the compound 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide, (L)-(+)-tartaric acid salt.

7. A kit according to claim 1 wherein the first pharmaceutical composition comprises the compound 2-amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, a prodrug thereof or a pharmaceutically acceptable salt of said compound or said prodrug.

8. A kit according to claim 7 wherein the first pharmaceutical composition comprises the compound 2-amino-N-(1(R)-benzyloxymethyl)-2-(1,3-dioxo-8a-(S)-pyridin-2-ylmethyl)-2-(2,2,2-trifluoro-ethyl)-hexahydro-imidazo[1,5-a]pyrazin-7-yl)-2-oxo-ethyl)-2-methyl-propionamide, (L)-(+)-tartaric acid salt.

9. A kit according to claim 1 wherein the prokinetic agent is selected from cisapride monohydrate, metoclopramide, erythromycin, domperidone, ondansetron, tropisetron, mosapride and itopride.

* * * * *